(12) United States Patent
Brown et al.

(10) Patent No.: US 7,547,749 B2
(45) Date of Patent: Jun. 16, 2009

(54) TRIAZINE COMPOUNDS, POLYMERS COMPRISING TRIAZINE STRUCTURAL UNITS, AND METHOD

(75) Inventors: Sterling Bruce Brown, Austin, TX (US); Hans-Peter Brack, Herrliberg (CH); James Anthony Cella, Clifton Park, NY (US); Dennis Karlik, Noord Brabant (NL)

(73) Assignee: SABIC Innovative Platics IP B.V., Bergen op Zoom (NL)

( * ) Notice: Subject to any disclaimer, the term of this patent is extended or adjusted under 35 U.S.C. 154(b) by 214 days.

(21) Appl. No.: 11/766,122

(22) Filed: Jun. 21, 2007

(65) Prior Publication Data

US 2008/0097040 A1 Apr. 24, 2008

Related U.S. Application Data

(60) Division of application No. 10/672,789, filed on Sep. 26, 2003, now Pat. No. 7,235,611, which is a continuation of application No. 09/941,050, filed on Aug. 28, 2001, now abandoned.

(51) Int. Cl.
*C08G 64/42* (2006.01)
*C08G 64/00* (2006.01)
*C08G 65/48* (2006.01)
*C08G 65/44* (2006.01)

(52) U.S. Cl. ........................ 525/391; 525/390; 525/392; 525/396; 525/467; 525/468

(58) Field of Classification Search ....................... None
See application file for complete search history.

(56) References Cited

U.S. PATENT DOCUMENTS 5,057,143 A * 10/1991 Rheinheimer et al. ....... 504/242

\* cited by examiner

*Primary Examiner*—David Buttner

(57) ABSTRACT

In various embodiments the present invention comprises 2,4,6-trisubstituted-1,3,5-triazine capping agents comprising one, two, or three leaving groups as substituents with any remaining substituents being essentially inert to reaction with a nucleophilic group on a polymer or monomer, or reactive with a nucleophilic group on a polymer or monomer at a slower rate than any leaving group. The invention also comprises polymers or monomers with nucleophilic groups capped with a triazine moiety. Still other embodiments of the invention comprise processes for capping nucleophilic groups in a polymer or monomer which comprises combining and reacting the polymer or monomer with a triazine-comprising capping agent.

9 Claims, No Drawings

TRIAZINE COMPOUNDS, POLYMERS COMPRISING TRIAZINE STRUCTURAL UNITS, AND METHOD

CROSS REFERENCE TO RELATED APPLICATIONS

This application is a Divisional of U.S. patent application Ser. No. 10/672,789 filed Sep. 26, 2003, now U.S. Pat. No. 7,235,611 which is a Continuation of U.S. patent application Ser. No. 09/941,050 filed Aug. 28, 2001 now abandoned, which is fully incorporated herein by reference.

BACKGROUND OF THE INVENTION

The present invention is directed to triazine compounds, polymers comprising triazine structural units, and methods for their preparation. More particularly, the present invention is directed to triazine compounds capable of reacting with nucleophilic groups on polymers or monomers; polymers which comprise at least one triazine moiety; and methods for preparing the polymers.

Many polymers as synthesized contain nucleophilic end-groups or nucleophilic groups as pendant groups in the chain of the polymer, or both. Nucleophilic end-groups may adversely affect the properties of the polymers when the polymers are used in certain applications. For example, the presence of hydroxy end-groups in poly(arylene ether)s may result in decreased thermal stability. Similarly, the presence of hydroxy end-groups in polycarbonates may result under certain circumstances in poorer color or optical hue, high surface static charging, sticking, and dust attraction after injection molding, poorer heat and water resistance, and poorer heat aging resistance. Polymers in which nucleophilic end-groups, particularly hydroxy end-groups, have been capped may exhibit improved properties compared to the corresponding polymers which have not been endcapped.

Capping of nucleophilic groups on polymers may be employed not only to improve physical properties but also to introduce into the polymer reactive functionality different from the initial nucleophilic group. For example introduction of epoxy, orthoester, or olefinic functional groups through capping with appropriate epoxy-, orthoester-, or olefin comprising capping agents may provide reactive polymers which may be used in various applications such as copolymer formation for compatibilization of immiscible polymer blends. Capping of nucleophilic groups on polymers may also result in chain-extension or branching of the polymers if a difunctional or trifunctional capping agent is used and more than one nucleophile-terminated chain participates in reaction. Also, capping of nucleophilic groups on polymers may result in cross-linked polymers if the nucleophilic groups comprise pendant groups and a difunctional or trifunctional capping agent is used. Chain-extended, branched, and cross-linked polymers often have improved properties such as increased melt strength for use in making blow molded articles.

Polymers endcapped through reaction with reactive triazine moieties have been reported. Nucleophile-terminated polymers such as hydroxy-terminated poly(arylene ether)s or hydroxy-terminated polycarbonates have been endcapped through reaction in solution with chlorotriazines as disclosed in U.S. Pat. Nos. 4,927,894, 5,034,527, 5,115,043, 5,132,373, 5,210,191, and 5,264,496. Nucleophile-terminated polymers such as amine-terminated polysiloxanes have been endcapped through reaction in solution with chlorotriazines as disclosed in U.S. Pat. No. 5,324,796. Branching of hydroxy-terminated poly(arylene ether)s using trichlorotriazine (also known as cyanuric chloride) in a solution reaction has been disclosed by White and Loucks in ACS Symposium Series, volume 282 (Reactive Oligomers), 187 (1985). Polycarbonates containing triazine structural units in the chain and also branched polycarbonates and molding compositions made therefrom have been disclosed in U.S. Pat. Nos. 3,957,728, 3,978,159, and 4,092,243. All of these references require that the incorporation of triazine structural units be carried out in a solution reaction in the presence of a base. The subsequent recovery of polymer typically requires antisolvent precipitation and drying of recovered polymer. Methods must be provided for solvent recovery and disposal of any salt derived from the base. A method is needed which provides a polymer with capped nucleophile groups in a melt process without the need for a base or recovery of large volumes of solvent.

Melt processes for endcapping of nucleophile-terminated polymers have been reported which rely on transesterification with a reactive ester. For example in U.S. Pat. No. 5,696,222 and in European Patent Application EP 703,261 hydroxy-terminated polycarbonate is capped through transesterification with a reactive ester. In one illustrative process a bisphenol and diphenylcarbonate (DPC) are used as reactants for synthesis of a polycarbonate in a melt transesterification process. Endcapping of hydroxy end-groups to yield phenyl-capped end-groups derived from DPC may be achieved by using a stoichiometric excess of DPC to give a desired endcap level and by driving the reaction equilibrium by applying a vacuum to remove the phenol byproduct. However, either excess DPC must be used at the beginning of the reaction or additional DPC must be added at a later reaction stage to compensate for the evaporative loss of the more volatile DPC reactant during later reaction stages at higher temperatures and pressures. Such use of excess DPC can give a higher endcap level, but these off-stoichiometry conditions sacrifice reaction rate and molecular weight. In addition, late addition of DPC is limited in effectiveness because of DPC's volatility under the later reaction conditions of higher temperature and lower pressure, and the DPC lost in later reaction stages must be separated from the phenol byproduct if they are to be recycled.

Another disadvantage is that the typical synthesis of a melt polycarbonate from a bisphenol and a diarylcarbonate such as DPC offers only the possibility of having unfunctionalized aryl end-groups on the polymer unless other monophenols are added early in the reaction or unless a post-reaction process is used. Adding a monophenol can change the end-group type, but may also adversely affect reaction rate and molecular weight of the polymer. Also added monophenols may be volatile under the reaction conditions. Also endcappers in post-reaction processes are often activated carbonates having a reactive leaving group which must be prepared using the toxic chemical phosgene and thus are not readily available at low cost.

A problem to be solved is to provide capping agents which are low cost, which react with nucleophile-containing monomers or with nucleophile-containing polymers during or subsequent to their synthesis, particularly in a melt process, and which release a species from the capping agent which in one embodiment may be easily removed, such as by devolatilization, and optionally recovered. In various embodiments it is also desirable that a capping agent impart some property improvement to a polymer composition, for example through removal of residual nucleophilic groups such as hydroxy groups, or through the presence of beneficial substituents on a capping agent attached to a polymer. In another embodiment it is desirable that a capping agent be capable of modification to introduce functionality into a nucleophile-containing polymer for subsequent reaction. In still another embodiment it is desirable that a capping agent be capable of reacting with a nucleophile-containing monomer as a participating species in a polymerization reaction. In still another embodiment it is desirable that a capping agent be employable in a manner such as to allow a polymerization to be carried out rapidly at close to stoichiometric conditions until a desired molecular weight is achieved and then to rapidly increase the endcap level and/or molecular weight to a desired level by adding an endcapping agent. In still another embodiment it is desirable that a capping agent be capable of modification to provide a chain-extension, branching, or cross-linking agent. After diligent experimentation the present inventors have discovered solutions to these problems.

SUMMARY OF THE INVENTION

In one embodiment the present invention comprises triazine-comprising capping agents of the formula (I):

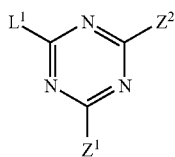

(I)

wherein $L^1$ is an aryloxy group comprising at least one electron withdrawing group ortho, meta, or para to the linkage between the aryloxy group and the triazine ring, and $Z^1$ and $Z^2$ are each independently groups which are essentially inert to reaction with a nucleophilic group on a polymer or monomer, or which react with a nucleophilic group on a polymer or monomer at a slower rate than the group, $L^1$.

In another embodiment the present invention comprises triazine-comprising capping agents of the formula (II):

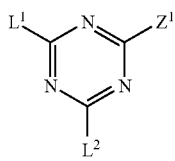

(II)

wherein $L^1$ and $L^2$ are each independently an aryloxy group comprising at least one electron withdrawing group ortho, meta, or para to the linkage between the aryloxy group and the triazine ring, and $Z^1$ is a group which is essentially inert to reaction with a nucleophilic group on a polymer or monomer, or which reacts with a nucleophilic group on a polymer or monomer at a slower rate than either of the groups, $L^1$ and $L^2$.

In another embodiment the present invention comprises triazine-comprising capping agents of the formula (III):

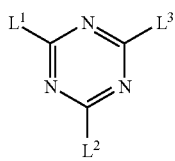

(III)

wherein $L^1$, $L^2$, and $L^3$ are each independently an aryloxy group comprising at least one electron withdrawing group ortho, meta, or para to the linkage between the aryloxy group and the triazine ring.

Other embodiments of the invention comprise polymers with nucleophilic groups capped with a triazine moiety. Still other embodiments of the invention comprise processes for synthesizing polymers comprising triazine-comprising capping agents.

Various other features, aspects, and advantages of the present invention will become more apparent with reference to the following description and appended claims.

DETAILED DESCRIPTION OF THE INVENTION

In the present context a polymer is a chemical species comprising at least two monomer units. In the present context a triazine-comprising capping agent is a triazine compound comprising at least one ring carbon atom reactive to a nucleophilic group on a second chemical species. In some embodiments a triazine-comprising capping agent is an endcapping agent. In one embodiment the present invention comprises triazine-comprising compounds which are capable of reacting with nucleophilic groups on polymers or monomers through a displacement reaction or in an exchange reaction such as a transesterification reaction or a transamidation reaction to provide reaction products comprising a triazine-comprising polymer and at least one leaving group derived from the triazine-comprising compound. In one embodiment the triazine-comprising polymer is an end-capped polymer comprising at least one triazine moiety as a terminal structural unit. Endcapped polymers in the present context include those comprising at least one triazine-comprising moiety as a terminal unit derived from reaction of a nucleophile-containing polymer with a monofunctional triazine-comprising capping agent, or derived from reaction of a nucleophile-containing monomer with a monofunctional triazine-comprising capping agent. Said monomer may be prereacted with monofunctional triazine-comprising capping agent in a separate reaction or may react with monofunctional triazine-comprising capping agent in the course of a polymerization reaction.

In another embodiment triazine-comprising polymers include those comprising at least one triazine-comprising moiety as a structural unit in a polymer chain other than at a terminal site. Such structural units may be derived from reaction of the nucleophile-containing polymer with a difunctional or with a trifunctional triazine-comprising capping agent. In the latter two embodiments the resulting polymers may comprise cyclic polymers when a single polymer chain with two nucleophilic end-groups reacts with difunctional or with trifunctional triazine-comprising capping agent; or chain-extended or branched polymers, when more than one nucleophile-terminated polymer chain reacts with difunctional or with trifunctional triazine-comprising capping agent, respectively. Triazine-comprising polymers which comprise at least one triazine-comprising moiety as a structural unit in the polymer chain other than at a terminal site may also be derived from reaction of a nucleophile-containing monomer with a difunctional or a trifunctional triazine-comprising capping agent. Said monomer may be prereacted with such a triazine-comprising capping agent in a separate reaction or may react with difunctional or trifunctional triazine-comprising capping agent in the course of a polymerization reaction.

Triazine-comprising polymers in the present context also include those comprising both at least one triazine-comprising moiety as a terminal unit and at least one triazine-comprising moiety as a structural unit in the polymer chain other than at a terminal site. In the present context a monofunctional triazine-comprising capping agent is one which reacts with a nucleophilic group predominantly at only one reactive site on the triazine ring; a difunctional triazine-comprising capping agent is one which reacts with a nucleophilic group predominantly at only two reactive sites on the triazine ring; and a trifunctional triazine-comprising capping agent is one which reacts with a nucleophilic group predominantly at three reactive sites on the triazine ring.

Nucleophilic groups include those known in the art, illustrative examples of which are hydroxy, thiohydroxy, amino, and carboxy (or carboxylate). In the present context the terms hydroxy and thiohydroxy include both aliphatic hydroxy or thiohydroxy groups and also aromatic hydroxy or thiohydroxy groups (the latter of which are sometimes referred to in the art as phenolic and thiophenolic groups, respectively).

Triazine-comprising compounds in various embodiments of the present invention include monofunctional triazine-comprising capping agents which are 2,4,6-trisubstituted-1,3,5-triazines of the formula (I):

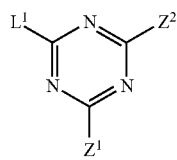

(I)

wherein $L^1$ is a leaving group reactive with a nucleophilic group on a polymer or monomer, and $Z^1$ and $Z^2$ are each independently groups which may be essentially inert to reaction with a nucleophilic group on a polymer or monomer, or which may react with a nucleophilic group on a polymer or monomer at a slower rate than the leaving group, $L^1$. In various embodiments $Z^1$ and $Z^2$ are the same. In other embodiments $Z^1$ and $Z^2$ are essentially inert under the reaction conditions and do not react with a nucleophilic group on a polymer or monomer.

Triazine-comprising compounds in other embodiments of the present invention include difunctional triazine-comprising capping agents which are 2,4,6-trisubstituted-1,3,5-triazines of the formula (II):

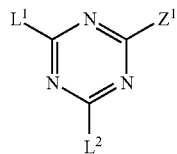

(II)

wherein $L^1$ and $L^2$ are each independently leaving groups reactive with a nucleophilic group on a polymer or monomer, and $Z^1$ is a group which may be essentially inert to reaction with a nucleophilic group on a polymer or monomer, or which may react with a nucleophilic group on a polymer or monomer at a slower rate than either of the leaving groups, $L^1$ and $L^2$. In certain embodiments $L^1$ and $L^2$ are the same. In other embodiments $Z^1$ is essentially inert under the reaction conditions and does not react with a nucleophilic group on a polymer or monomer.

Triazine-comprising compounds in other embodiments of the present invention include trifunctional triazine-comprising capping agents which are 2,4,6-trisubstituted-1,3,5-triazines of the formula (III):

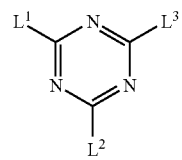

(III)

wherein $L^1$, $L^2$, and $L^3$ are each independently leaving groups reactive with a nucleophilic group on a polymer or monomer. In certain embodiments $L^1$, $L^2$, and $L^3$ are the same.

In various embodiments L (as embodied in $L^1$, $L^2$, and $L^3$) is halo, chloro or an aryloxy group comprising at least one electron withdrawing group ortho, meta, or para to the linkage between the aryloxy group and the triazine ring. In one embodiment L is an aryloxy group comprising at least one electron withdrawing group ortho or para to the linkage between the aryloxy group and the triazine ring. In another embodiment L is an aryloxy group comprising at least one electron withdrawing group ortho or para to the linkage between the aryloxy group and the triazine ring selected from the group consisting of carboalkoxy, carboaryloxy, carboaryl, halo, cyano, and nitro, and mixtures thereof. In another embodiment L is selected from the group consisting of o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy.

In one embodiment leaving groups, L, are volatile and may be removed from a reaction mixture by devolatilization as leaving group compound. Removal of leaving group compound from a reaction mixture also serves to drive the equilibrium in favor of polymer or monomer comprising triazine structural units. If desired, leaving group compound may be recovered and recycled for further use. Leaving groups, L, may, if desired, also have substituents such as alkyl, aryl, alkaryl, aralkyl, alkoxy, aryloxy, silyl, halo, or fluoro substituents to assist in regulating the molecular weight and volatility of the triazine comprising compound or the leaving group compound, or both. For example aryloxy groups comprising at least one electron-withdrawing substituent may, if desired, also have substituents such as alkyl, aryl, alkaryl, aralkyl, alkoxy, aryloxy, silyl, halo, or fluoro substituents to assist in regulating the molecular weight and volatility of the triazine comprising compound or the leaving group L, or both.

In various embodiments Z (as embodied in $Z^1$ and $Z^2$) is at least one of alkyl, aryl, alkaryl, aralkyl, alkoxy, aryloxy, alkylamino, or arylamino group, illustrative non-limiting examples of which include substituted aryloxy, arylaryloxy, arylphenoxy, alkylphenoxy (for example, 2-alkylphenoxy, 3-alkylphenoxy, and 4-alkylphenoxy), dialkylphenoxy (for example, 2,6-dialkylphenoxy, 2,3-dialkylphenoxy, 2,5-dialkylphenoxy, 2,4-dialkylphenoxy, 3,4-dialkylphenoxy, and 3,5-dialkylphenoxy), cyanophenoxy, halophenoxy, dihalophenoxy (for example, 2,6-dihalophenoxy, 2,3-dihalophenoxy, 2,5-dihalophenoxy, 2,4-dihalophenoxy, 3,4-dihalophenoxy, and 3,5-dihalophenoxy), 2,6-dialkoxycarbonylphenoxy, trialkylphenoxy (for example, 2,3,4-trialkylphenoxy, 2,3,5-trialkylphenoxy, 2,3,6-trialkylphenoxy, 2,4,5-trialkylphenoxy, 3,4,5-trialkylphenoxy, and 2,4,6-trialkylphenoxy), trihalophenoxy (for example, 2,3,4-trihalophenoxy, 2,3,5-trihalophenoxy, 2,3,6-trihalophenoxy, 2,4,5-trihalophenoxy, 3,4,5-trihalophenoxy, and 2,4,6-trihalophenoxy), and their tetra-substituted analogs. The aryloxy or arylamino groups may be also be deactivated or rendered essentially inert towards reaction with a nucleophilic group on a polymer or monomer by means of electron-donating groups, illustrative examples of which include alkoxy. Thus, in illustrative embodiments Z (as embodied in $Z^1$ and $Z^2$) includes alkoxyphenoxy, dialkoxyphenoxy, and trialkoxyphenoxy. Other examples of essentially inert groups suitable for Z may be found in U.S. Pat. No. 5,696,222.

A triazine-comprising capping agent may also comprise a functionality which is incorporated into a nucleophile-containing polymer or monomer when the polymer or monomer reacts with the triazine-comprising capping agent. Illustrative triazine capping agents of this type are depicted in formulas (IV)-(VI):

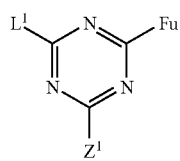

(IV)

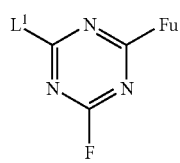

(V)

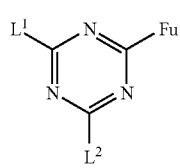

(VI)

wherein $L^1$, $L^2$, and $Z^1$ are as defined above and Fu represents a functional group which may be essentially inert to reaction or which may react with a nucleophilic group on a polymer or monomer at a slower rate than a leaving group, L. In one embodiment of formula (V) each Fu group is the same. In one embodiment of formula (VI) $L^1$ and $L^2$ are the same. Illustrative examples of functional groups, Fu, include vinyl, allyl, propargyloxy, and olefinic groups as illustrated by formula (VII; $Fu^1$), epoxy groups as illustrated by formula (VIII; $Fu^2$), and cyclic orthoester groups as illustrated by formula (IX; $Fu^3$):

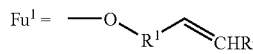

(VII)

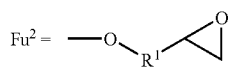

(VIII)

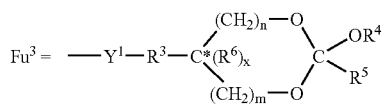

(IX)

wherein $R^1$ is alkyl or aryl; $R^2$ is hydrogen, alkyl, or aryl; $Y^1$ is nitrogen or oxygen; $R^3$ is a $C_{1-6}$ alkylene radical, and $R^4$ is a $C_{1-4}$ primary or secondary alkyl radical or is an alkylene radical forming a second 5- or 6-membered ring with C*, $R^5$ is a $C_{1-4}$ primary or secondary alkyl or $C_{6-10}$ aromatic radical, or $R^4$ and $R^5$ together with the atoms connecting them form a 5-, 6-, or 7-membered ring; $R^6$ is hydrogen or a $C_{1-4}$ primary or secondary alkyl; m is zero or one, and n is from 1 to 2m; and x is zero when $R^4$ and C* form a ring and is otherwise one.

In the context of the present invention alkyl radicals or groups are those containing from 1 to about 30 carbon atoms, and include straight chain alkyl radicals, branched alkyl radicals and cycloalkyl radicals. Alkyl radicals may contain one or more unsaturated groups. Some illustrative non-limiting examples of alkyl radicals include methyl, ethyl, propyl, isopropyl, allyl, butyl, tertiary-butyl, pentyl, neopentyl, hexyl, hexenyl, octyl, nonyl, decyl, dodecyl, dodecenyl, pentadecyl, pentadecenyl, hexadecyl, octadecyl, oleyl, lauryl, palmityl, and stearyl. Cycloalkyl radicals or groups are typically those containing from 3 to about 12 ring carbon atoms. Some illustrative non-limiting examples of cycloalkyl radicals include cyclobutyl, cyclopentyl, cyclohexyl, methylcyclohexyl, and cycloheptyl. Alkylamino radicals include those of the formula $R^1R^2N$— wherein $R^1$ and $R^2$ are each independently an alkyl group as defined above, or wherein $R^1$ and $R^2$ are part of a heterocyclic ring system, illustrative examples of which include pyrrolidyl, piperidyl, and morpholinyl. Aryl radicals or groups (and consequently arylamino and aryloxy groups) in the present context may be either substituted or unsubstituted, and are typically all-carbon ring systems or heteroaromatic ring systems containing from 4 to 14 ring carbon atoms. Some illustrative non-limiting examples of aryl radicals include furyl, chromanyl, phenyl, biphenyl, naphthyl, and anthranyl. Substituted aryl radicals are not limited as to position of substitution provided that a triazine-comprising moiety comprising the substituted aryl radical can be prepared. Thus, in the case of phenyl radicals (and consequently phenylamino and phenoxy groups) a substituent may be in the ortho, meta, or para position. Typical aralkyl and alkaryl radicals or groups are those containing from 7 to about 24 carbon atoms. These include, but are not limited to, benzyl, ethylphenyl, phenylbutyl, phenylpropyl, propylphenyl, and phenylethyl. In illustrative embodiments of the invention $R^1$ is methylene and $R^2$ is hydrogen wherein $Fu^1$ is derived from allyl alcohol; $R^1$ is phenyl and $R^2$ is hydrogen wherein $Fu^1$ is derived from 4-hydroxystyrene; $R^1$ is ethylene and $R^2$ is phenyl wherein $Fu^1$ is derived from cinnamyl alcohol; $R^1$ is phenyl-2-methylene or phenyl-4-methylene and $R^2$ is hydrogen wherein $Fu^1$ is derived from 2- or 4-allylphenol, respectively; or $R^1$ is 2-methoxyphenyl-4-methylene and $R^2$ is hydrogen wherein $Fu^1$ is derived from eugenol. In other embodiments of the invention $R^1$ is methylene wherein $Fu^2$ is derived from glycidol. In other embodiments of the invention $R^3$ is methylene, ethylene, propylene, tetramethylene, pentamethylene, or hexamethylene; and $R^4$ is methyl, ethyl, n-propyl, isopropyl, n-butyl, isobutyl, or sec-butyl. In various embodiments the cyclic orthoester moiety is a five membered ring in which m is zero and n is one; or a six-membered ring in which either m and n are both one, or m is zero and n is two. Illustrative examples of cyclic orthoester moieties of formula (IX) include those of formulas (X) and (XI):

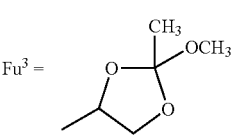

(X)

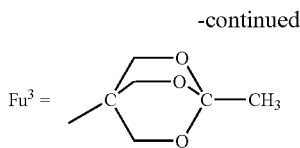

(XI)

Formula (X) is the 4-(2-methoxy-2-methyl-1,3-dioxolanyl) radical. In one embodiment said radical may be derived from 4-hydroxymethyl-2-methoxy-2-methyl-1,3-dioxolane (and is hereinafter sometimes referred to as 4-oxymethyl-2-methoxy-2-methyl-1,3-dioxolane radical) which is obtainable by the reaction of glycerol and methyl orthoacetate. Formula (XI) is the 4-(1-methyl-2,6,7-trioxabicyclo[2.2.2] octyl) radical and in one embodiment the methylol derivative may be prepared by the reaction of ethyl orthoacetate with pentaerythritol.

Illustrative, non-limiting embodiments of monofunctional triazine-comprising capping agents include compounds of the formula (I) in which $L^1$ is selected from the group consisting of chloro, o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy; and $Z^1$ and $Z^2$ are each independently selected from the group consisting of methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, 4-cumylphenoxy, 4-(1,1,3,3-tetramethylbutyl) phenoxy, octylphenoxy, 4-tert-octylphenoxy, nonylphenoxy, dodecylphenoxy, octadecylphenoxy, pentadecylphenoxy, pentadecenylphenoxy, 2-methoxyethylphenoxy, 4-(4'-oxyphenyl)-2,2,4-trimethylchroman, 2-(4'-oxyphenyl)-2,4,4-trimethyl chroman, 1-(1-methyl-1-phenylethyl)-4-(1-methyl-1-(4'-oxyphenyl)ethyl)-benzene, phenylphenoxy, naphthylphenoxy, 1,3-bis(1-methyl-1-phenylethyl)-5-(1-methyl-1-(4'-oxyphenyl)ethyl)-benzene, 4-cyanophenoxy, 4-halophenoxy, 4-bromophenoxy, methoxyphenoxy, phenoxyphenoxy, benzyloxyphenoxy, n-hexyloxyphenoxy, dimethoxyphenoxy, 2,6-dimethylphenoxy, 2,6-di-t-butylphenoxy, 3,5-di-t-butylphenoxy, 3,5-dicumylphenoxy, 2,4-di-t-butylphenoxy, 2,5-di-t-butylphenoxy, 2,5-dicumylphenoxy, 2,3-di-t-butylphenoxy, dibromophenoxy, 2,6-dibromophenoxy, 2,6-dichlorophenoxy, 2,6-(dimethoxycarbonyl)phenoxy, 2,3,6-trimethylphenoxy, 2,4,6-trimethylphenoxy, tribromophenoxy, 2,4,6-tribromophenoxy, and 2,4,6-trichlorophenoxy.

The radicals 4-(4'-oxyphenyl)-2,2,4-trimethylchroman and 2-(4'-oxyphenyl)-2,4,4-trimethylchroman are derived from compounds (XII) and (XIII), respectively:

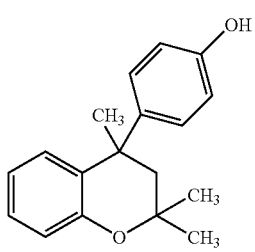

(XII)

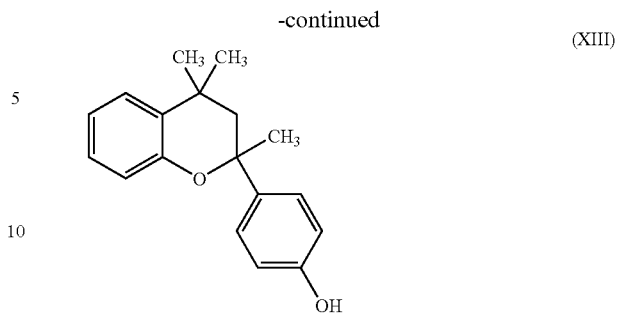

(XIII)

The radicals 1-(1-methyl-1-phenylethyl)-4-(1-methyl-1-(4'-oxyphenyl)ethyl)-benzene and 1,3-bis(1-methyl-1-phenylethyl)-5-(1-methyl-1-(4'-oxyphenyl)ethyl)benzene are derived from compounds (XIV) and (XV), respectively:

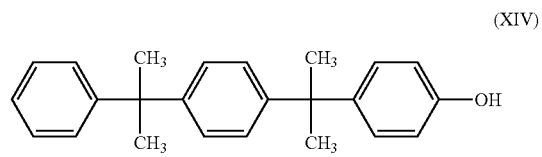

(XIV)

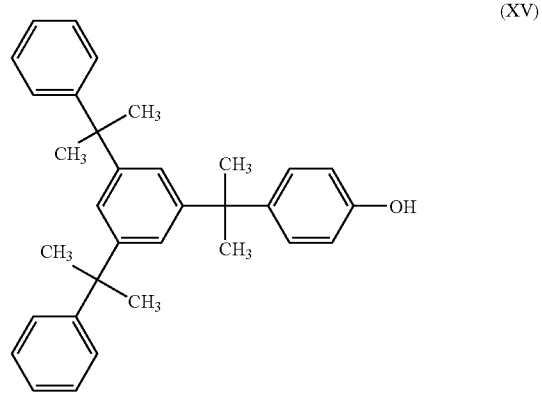

(XV)

Illustrative embodiments of monofunctional triazine-comprising capping agents also include compounds of the formulas (IV) and (V) in which $L^1$ is selected from the group consisting of chloro, o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy; $Z^1$, if present, is selected from the group consisting of methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, 4-cumylphenoxy, 4-(1,1,3,3-tetramethylbutyl)phenoxy, octylphenoxy, 4-tert-octylphenoxy, nonylphenoxy, dodecylphenoxy, octadecylphenoxy, pentadecylphenoxy, pentadecenylphenoxy, 2-methoxyethylphenoxy, 4-(4'-oxyphenyl)-2,2,4-trimethylchroman, 2-(4'-oxyphenyl)-2,4,4-trimethylchroman, 1-(1-methyl-1-phenylethyl)-4-(1-methyl-1-(4'-oxyphenyl)ethyl)-benzene, phenylphenoxy, naphthylphenoxy, 1,3-bis(1-methyl-1-phenylethyl)-5-(1-methyl-1-(4'-oxyphenyl)ethyl)-benzene, 4-cyanophenoxy, 4-halophenoxy, 4-bromophenoxy, methoxyphenoxy, phenoxyphenoxy, benzyloxyphenoxy, n-hexyloxyphenoxy, dimethoxyphenoxy, 2,6-dimethylphenoxy, 2,6-di-t-butylphenoxy, 3,5-di-t-butylphenoxy, 3,5-dicumylphenoxy, 2,4-di-t-butylphenoxy, 2,5-di-t-butylphenoxy, 2,5-dicumylphenoxy, 2,3-di-t-butylphenoxy, dibromophenoxy, 2,6-dibromophenoxy, 2,6-dichlorophenoxy, 2,6-(dimethoxycarbonyl)phenoxy, 2,3,6-trimethylphenoxy, 2,4,6-trimethylphenoxy, tribromophenoxy, 2,4,6-tribromophenoxy, and 2,4,6-trichlorophenoxy; and Fu is selected from the group consisting of vinyl, allyl, allyloxy, 2-allylphenoxy, 4-allylphenoxy, 4-ethenylphenoxy, cinnamyloxy, 4-allyl-2-methoxyphenoxy, propargyloxy, glycidoxy, and 4-(2-methoxy-2-methyl-1,3-dioxolanyl)methoxy 4-oxymethyl-2-methoxy-2-methyl-1,3-dioxolane.

Illustrative embodiments of difunctional triazine-comprising capping agents include compounds of the formula (II) in which $L^1$ and $L^2$ are each independently selected from the group consisting of o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy; and $Z^1$ is selected from the group consisting of methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, 4-cumylphenoxy, 4-(1,1,3,3-tetramethylbutyl)phenoxy, octylphenoxy, 4-tert-octylphenoxy, nonylphenoxy, dodecylphenoxy, octadecylphenoxy, pentadecylphenoxy, pentadecenylphenoxy, 2-methoxyethylphenoxy, 4-(4'-oxyphenyl)-2,2,4-trimethylchroman, 2-(4'-oxyphenyl)-2,4,4-trimethylchroman, 1-(1-methyl-1-phenylethyl)-4-(1-methyl-1-(4'-oxyphenyl)ethyl)-benzene, phenylphenoxy, naphthylphenoxy, 1,3-bis(1-methyl-1-phenylethyl)-5-(1-methyl-1-(4'-oxyphenyl)ethyl)-benzene, 4-cyanophenoxy, 4-halophenoxy, 4-bromophenoxy, methoxyphenoxy, phenoxyphenoxy, benzyloxyphenoxy, n-hexyloxyphenoxy, dimethoxyphenoxy, 2,6-dimethylphenoxy, 2,6-di-t-butylphenoxy, 3,5-di-t-butylphenoxy, 3,5-dicumylphenoxy, 2,4-di-t-butylphenoxy, 2,5-di-t-butylphenoxy, 2,5-dicumylphenoxy, 2,3-di-t-butylphenoxy, dibromophenoxy, 2,6-dibromophenoxy, 2,6-dichlorophenoxy, 2,6-(dimethoxycarbonyl)phenoxy, 2,3,6-trimethylphenoxy, 2,4,6-trimethylphenoxy, tribromophenoxy, 2,4,6-tribromophenoxy, and 2,4,6-trichlorophenoxy. Illustrative embodiments of difunctional triazine-comprising capping agents also include compounds of the formula (VI) in which $L^1$ and $L^2$ are each independently selected from the group consisting of chloro, o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy; and Fu is selected from the group consisting of vinyl, allyl, allyloxy, 2-allylphenoxy, 4-allylphenoxy, 4-ethenylphenoxy, cinnamyloxy, 4-allyl-2-methoxyphenoxy, propargyloxy, glycidoxy, and 4-oxymethyl-2-methoxy-2-methyl-1,3-dioxolane.

Illustrative embodiments of trifunctional triazine-comprising capping agents include compounds of the formula (III) in which $L^1$, $L^2$, and $L^3$ are each independently selected from the group consisting of o-carbomethoxyphenoxy, o-carbomethoxymethylphenoxy, o-carboethoxyphenoxy, o-carbopropoxyphenoxy, o-chlorophenoxy, o-carbophenylphenoxy, o-carbophenoxyphenoxy, o-carbobenzoxyphenoxy, and o-nitrophenoxy. In one embodiment $L^1$, $L^2$, and $L^3$ are each 2-carbomethoxyphenoxy.

Methods of making triazine-comprising compounds of the present invention include those methods known in the art. In various embodiments cyanuric chloride (2,4,6-trichloro-1,3, 5-triazine) is contacted under reactive conditions with precursors for Z (if present), Fu (if present), and L. In one embodiment the precursors are contacted with cyanuric chloride sequentially in the order: Z, followed by Fu, followed by L. In another embodiment the precursors are contacted with cyanuric chloride sequentially in the order: Fu, followed by Z, followed by L. In another embodiment the precursors are contacted with cyanuric chloride sequentially in the order: Z, followed by L. Examples of precursors include derivatives of alcohols, amines, phenols, and anilines. Reactive conditions generally comprise the presence of a solvent and an acid-acceptor for hydrochloric acid which is typically released upon reaction of cyanuric chloride with precursor compounds. In one embodiment the acid-acceptor comprises aqueous sodium hydroxide and the reaction is carried out in a two-phase mixture of water and organic solvent, in which case a phase transfer catalyst may optionally be present. Phase transfer catalysts are well-known in the art and include quaternary ammonium and phosphonium compounds. In another embodiment the acid acceptor comprises a tertiary amine. In another embodiment the acid-acceptor comprises sodium hydride and the reaction is carried out in an organic solvent. In various embodiments a process step is included for separation of salt.

Nucleophile-containing polymers of the present invention comprise all those known in the art capable of being processed under solution, melt, or slurry conditions, such as, but not limited to, nucleophile-containing thermoplastic, thermoplastic-elastomeric, or elastomeric resins, or oligomers. Illustrative examples include, but are not limited to, nucleophile-terminated polyethers, poly(arylene ether)s, poly(phenylene ether)s, poly(2,6-dimethylphenylene ether)s, polyethersulfones, polyetheresters, polyetherimides, polyamideimides, polyimides, polyetherketones, polyaryletherketones, polyetheretherketones, polyetherketoneketones, poly(arylene sulfide)s, poly(phenylene sulfide)s, polyacetals, polycarbonates, polyesters, poly(alkylene terephthalate)s, polyarylates, liquid crystalline polyesters, polyestercarbonates, polysulfones, polyethylene glycols, polypropylene glycols, polyethylene-propylene glycols, oxidized polyolefins, siloxanes, amine-terminated siloxanes, and hydroxy-terminated siloxanes such as eugenol-capped siloxanes. Illustrative examples also include polymers with nucleophilic groups pendant in the polymer chain such as hydroxy-containing siloxanes, amine-containing siloxanes, copolymers containing hydroxyalkylacrylates, oxidized polyolefins, and phenoxy resins. Nucleophile-containing monomers in the present context comprise those suitable for making nucleophile-containing polymers of the present invention. In various embodiments nucleophile-containing monomers of the present invention comprise those which may participate in a condensation polymerization reaction to make nucleophile-containing polymers of the present invention.

In one embodiment the present invention comprises poly(phenylene ether)s which comprise triazine structural units. Poly(phenylene ether)s (sometimes referred to hereinafter as "PPE") are known polymers comprising a plurality of structural units of the formula (XVI):

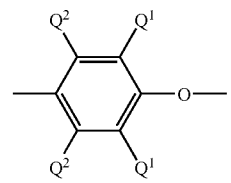

(XVI)

wherein in each of said units independently, each $Q^1$ is independently halogen, primary or secondary lower alkyl (i.e., alkyl containing up to 7 carbon atoms), phenyl, haloalkyl, aminoalkyl, hydrocarbonoxy, or halohydrocarbonoxy wherein at least two carbon atoms separate the halogen and oxygen atoms; and each $Q^2$ is independently hydrogen, halogen, primary or secondary lower alkyl, phenyl, haloalkyl, hydrocarbonoxy or halohydrocarbonoxy as defined for $Q^1$. In certain embodiments each $Q^1$ is alkyl or phenyl, especially $C_{1-4}$ alkyl, and each $Q^2$ is hydrogen.

Both homopolymer and copolymer poly(phenylene ether)s are included. In one embodiment homopolymers are those containing 2,6-dimethyl-1,4-phenylene ether units. In one embodiment suitable copolymers include random or block copolymers containing 2,6-dimethyl-1,4-phenylene ether units in combination with (for example) 2,3,6-trimethyl-1,4-phenylene ether units. Also included within this class of polymers are those produced by copolymerization of at least one monophenol such as 2,6-dimethylphenol and a polyfunctional phenol such as the bisphenol, 2,2-bis(3,5-dimethyl-4-hydroxyphenyl)propane, so as to produce a bifunctional phenol-containing polymer. Typical polyfunctional phenols, and the resulting poly(phenylene ether) polymers produced from them, include those described in U.S. Pat. No. 5,352,745. Also included are poly(phenylene ether)s containing moieties prepared by grafting onto the poly(phenylene ether) in known manner such materials as vinyl monomers or polymers such as polystyrenes and elastomers, as well as coupled poly(phenylene ether)s in which coupling agents such as low molecular weight polycarbonates, quinones, heterocycles and formals undergo reaction in known manner with the hydroxy groups of two poly(phenylene ether) chains to produce a higher molecular weight polymer, provided that at least a portion of hydroxy groups remains available for reaction with triazine moieties.

The poly(phenylene ether)s have an intrinsic viscosity (IV) in one embodiment greater than about 0.08, in another embodiment greater than about 0.25, in another embodiment in the range of about 0.25-0.6 and in still another embodiment in the range of 0.4-0.6 dl./g., as measured in chloroform at 25° C. Mixtures of poly(phenylene ether)s with different intrinsic viscosities are also suitable for use in the compositions of the invention. Such mixtures include those containing both low and high intrinsic viscosity poly(phenylene ether) resins such as is illustrated by 0.12 IV resin in combination with 0.46 IV resin.

The poly(phenylene ether)s are typically prepared by the oxidative coupling of reactants comprising at least one monohydroxyaromatic compound such as 2,6-xylenol or 2,3,6-trimethylphenol. Catalyst systems are generally employed for such coupling; they typically contain at least one heavy metal compound such as a copper, manganese or cobalt compound, usually in combination with various other materials. Illustrative examples of catalysts and processes are disclosed in U.S. Pat. Nos. 3,306,874, 3,306,875, 3,914,266, 4,028,341, 4,054,553, 4,092,294, 4,477,651, and 4,517,341.

In some embodiments poly(phenylene ether)s as synthesized contain at least one aminoalkyl-containing end group. The aminoalkyl radical is typically located in an ortho position to the hydroxy group. Poly(phenylene ether)s containing such end groups may be obtained by incorporating an appropriate primary or secondary monoamine such as di-n-butylamine or dimethylamine as one of the constituents of the oxidative coupling reaction mixture. Also frequently present are 4-hydroxybiphenyl end groups, typically obtained from reaction mixtures in which a byproduct diphenoquinone is present, especially in a copper-halide-secondary or tertiary amine system. In one embodiment a substantial proportion of the poly(phenylene ether) molecules, typically constituting as much as about 90% by weight of the polymer, may contain at least one of said aminoalkyl-containing and 4-hydroxybiphenyl end groups.

In various embodiments low molecular weight PPE polymers may be desirable to provide higher levels of phenol terminal-groups, enhance flow, improve processability, or provide suitable homogeneity with other blend components. Low molecular weight PPE polymers have in various embodiments a number average molecular weight (Mn; as measured in chloroform at 25° C. versus polystyrene standards) of between about 1,200 and about 9,700; in other embodiments the Mn is between about 2,100 and about 5,900; and in still other embodiments the Mn is between about 2,100 and about 3,900. As described above, these low molecular weight PPE polymers may be produced by oxidative polymerization. Alternatively, low molecular weight PPE polymers may be produced by other known methods such as by redistribution of PPE with a phenolic compound in the presence of an oxidizing agent.

It will be apparent to those skilled in the art from the foregoing that the poly(phenylene ether)s contemplated for use in the present invention include all those presently known which have nucleophilic groups, particularly nucleophilic end-groups, irrespective of variations in structural units or ancillary chemical features.

In another embodiment the present invention comprises polycarbonates which comprise triazine structural units. In various embodiments polycarbonates of the present invention comprise structural units derived from at least one triazine-comprising compound, at least one dihydric phenol and a carbonate precursor. Suitable dihydric phenols include those represented by the formula (XVII):

HO-D-OH                                                              (XVII)

wherein D is a divalent aromatic radical. In various embodiments D has the structure of formula (XVIII);

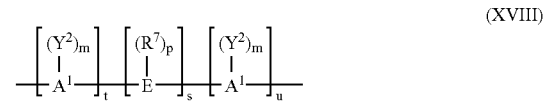

(XVIII)

wherein $A^1$ represents an aromatic group such as phenylene, biphenylene, naphthylene, etc. E may be an alkylene or alkylidene group including, but not limited to, methylene, ethylene, ethylidene, propylene, propylidene, isopropylidene, butylene, butylidene, isobutylidene, amylene, amylidene, isoamylidene. When E is an alkylene or alkylidene group, it may also consist of two or more alkylene or alkylidene groups connected by a moiety different from alkylene or alkylidene, such as an aromatic linkage; a tertiary amino linkage; an ether linkage; a carbonyl linkage; a silicon-containing linkage; or a sulfur-containing linkage including, but not limited to, sulfide, sulfoxide, sulfone; or a phosphorus-containing linkage including, but not limited to, phosphinyl, phosphonyl. In addition, E may be a cycloaliphatic group including, but not limited to, cyclopentylidene, cyclohexylidene, 3,3,5-trimethylcyclohexylidene, methylcyclohexylidene, 2-[2.2.1]-bicycloheptylidene, neopentylidene, cyclopentadecylidene, cyclododecylidene, adamantylidene; a sulfur-containing linkage, such as sulfide, sulfoxide or sulfone; a phosphorus-containing linkage, such as phosphinyl or phosphonyl; an ether linkage; a carbonyl group; a tertiary nitrogen group; or a silicon-containing linkage such as silane or siloxy. $R^7$ represents hydrogen or a monovalent hydrocarbon group such as alkyl, aryl, aralkyl, alkaryl, or cycloalkyl. In various embodiments a monovalent hydrocarbon group of $R^7$ may be halogen-substituted, particularly fluoro- or chloro-substituted, for example as in dichloroalkylidene. $Y^2$ may be an inorganic atom including, but not limited to, halogen (fluorine, bromine, chlorine, iodine); an inorganic group including, but not limited to, nitro; an organic group including, but not limited to, a monovalent hydrocarbon group such as alkyl, aryl, aralkyl, alkaryl, or cycloalkyl, or an oxy group such as $OR^8$, wherein $R^8$ is a monovalent hydrocarbon group such as alkyl, aryl, aralkyl, alkaryl, or cycloalkyl; it being only necessary that $Y^2$ be inert to and unaffected by the reactants and reaction conditions used to prepare a polycarbonate. The letter "m" represents any integer from and including zero through the number of positions on $A^1$ available for substitution; "p" represents an integer from and including zero through the number of positions on E available for substitution; "f" represents an integer equal to at least one; "s" is either zero or one; and "u" represents any integer including zero.

When more than one $Y^2$ substituent is present as represented by formula (XVIII) above, they may be the same or different. When more than one $R^7$ substituent is present, they may be the same or different. Where "s" is zero in formula (XVIII) and "u" is not zero, the aromatic rings are directly joined with no intervening alkylidene or other bridge. The positions of the hydroxyl groups and $Y^2$ on the aromatic residues $A^1$ can be varied in the ortho, meta, or para positions and the groupings can be in vicinal, asymmetrical or symmetrical relationship, where two or more ring carbon atoms of the aromatic residue are substituted with $Y^2$ and hydroxyl groups.

Some illustrative, non-limiting examples of dihydric phenols of formula (XVII) include the dihydroxy-substituted aromatic hydrocarbons disclosed by name or formula (generic or specific) in U.S. Pat. No. 4,217,438. In various embodiments of the invention dihydric phenols include 6-hydroxy-1-(4'-hydroxyphenyl)-1,3,3-trimethylindane, 4,4'-(3,3,5-trimethylcyclohexylidene)diphenol; 1,1-bis(4-hydroxy-3-methylphenyl)cyclohexane; 2,2-bis(4-hydroxyphenyl)propane (commonly known as bisphenol-A or "BPA"); 2,2-bis(4-hydroxy-3,5-dimethylphenyl)propane; 2,2-bis(4-hydroxy-3-methylphenyl)propane; 2,2-bis(4-hydroxy-3-ethylphenyl)propane; 2,2-bis(4-hydroxy-3-isopropylphenyl) propane; 2,4'-dihydroxydiphenylmethane; bis(2-hydroxyphenyl)methane; bis(4-hydroxy-phenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)ethane; 2,2-bis(3-phenyl-4-hydroxyphenyl)-propane; bis(4-hydroxyphenyl)cyclohexylmethane; 2,2-bis(4-hydroxyphenyl)-1-phenylpropane; hydroquinone, resorcinol; $C_{1-3}$ alkyl-substituted resorcinols.

Suitable dihydric phenols also include those containing indane structural units such as represented by the formula (XIX), which compound is 3-(4-hydroxyphenyl)-1,1,3-trimethylindan-5-ol, and by the formula (XX), which compound is 1-(4-hydroxyphenyl)-1,3,3-trimethylindan-5-ol:

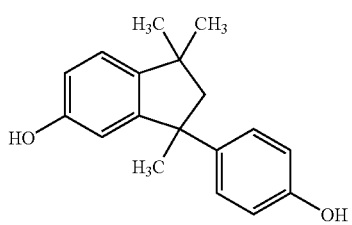

(XIX)

-continued

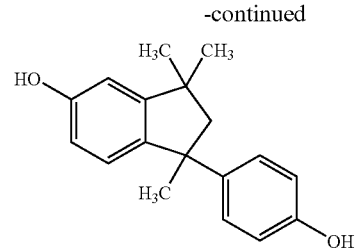

(XX)

Suitable dihydric phenols also include those containing spirobiindane structural units such as represented by the formula (XXI):

(XXI)

wherein each $R^{20}$ is independently selected from monovalent hydrocarbon radicals and halogen radicals; each $R^{21}$, $R^{22}$, $R^{23}$, and $R^{24}$ is independently $C_{1-6}$ alkyl; each $R^{25}$ and $R^{26}$ is independently H or $C_{1-6}$ alkyl; and each n is independently selected from positive integers having a value of from 0 to 3 inclusive. The monovalent hydrocarbon radicals represented by $R^{20}$ include alkyl radicals, cycloalkyl radicals, aryl radicals, aralkyl radicals, and alkaryl radicals, as already defined hereinabove. In various embodiments the halogen radicals represented by $R^{20}$ are fluorine, chlorine and bromine.

In the dihydric phenol compound of formula (XXI) when more than one $R^{20}$ substituent is present they may be the same or different. The relative positions of the hydroxyl groups and $R^{20}$ on the aromatic nuclear residues may be varied in the ortho or meta positions. The position of each hydroxy group is independently at any unsubstituted site on each of the aromatic rings. In one embodiment each hydroxy group is independently in positions 5 or 6 and 5' or 6' of each aromatic ring. In another embodiment each hydroxy group is in position 6 and 6' of each aromatic ring.

In various embodiments, each $R^{20}$ is independently selected from chlorine, bromine, and lower alkyl radicals containing from 1 to about 5 carbon atoms, each $R^{21}$, $R^{22}$, $R^{23}$, and $R^{24}$ is independently $C_{1-6}$ alkyl; each $R^{25}$ and $R^{26}$ is independently H or $C_{1-6}$ alkyl; and each n is independently 0 to 3. In some embodiments, each $R^{20}$ is independently selected from chlorine and lower alkyl radicals containing from 1 to about 3 carbon atoms, each $R^{21}$, $R^{22}$, $R^{23}$, and $R^{24}$ is independently $C_{1-2}$ alkyl; each $R^{25}$ and $R^{26}$ is independently H or $C_{1-2}$ alkyl; and each n is independently 0 to 2. In other embodiments, each $R^{21}$, $R^{22}$, $R^{23}$, and $R^{24}$ is methyl; each $R^{25}$ and $R^{26}$ is H; and each n is 0.

In one embodiment a spiro dihydric phenol for forming polycarbonates suitable for use in the present invention is 6,6'-dihydroxy-3,3,3',3'-tetramethyl-1,1'-spirobiindane (sometimes know as "SBI"), in which n in formula (XXI) is 0 and the linkages with the rest of the polymer molecule are in a specific position on the aromatic rings.

In various embodiments the carbonate precursor for preparing polycarbonates include at least one carbonyl halide, carbonate ester or haloformate. The carbonyl halides which can be employed herein are carbonyl chloride, carbonyl bromide and mixtures thereof. Typical carbonate esters which may be employed herein include, but are not limited to, diaryl carbonates, including, but not limited to, diphenylcarbonate, di(halophenyl)carbonates, di(chlorophenyl)carbonate, di(bromophenyl)carbonate, di(trichlorophenyl)carbonate, di(tribromophenyl)carbonate; di(alkylphenyl)carbonates, di(tolyl)carbonate; di(naphthyl)carbonate, di(chloronaphthyl)carbonate, phenyl tolyl carbonate, chlorophenyl chloronaphthyl carbonate, di(methyl salicyl)carbonate, and mixtures thereof. The haloformates suitable for use herein include bishaloformates of dihydric phenols, which include, but are not limited to, bischloroformates of hydroquinone; bisphenol-A; 3-(4-hydroxyphenyl)-1,1,3-trimethylindan-5-ol; 1-(4-hydroxyphenyl)-1,3,3-trimethylindan-5-ol; 4,4'-(3,3,5-trimethylcyclohexylidene)diphenol; 1,1-bis(4-hydroxy-3-methylphenyl)cyclohexane, and the like; bischloroformate-terminated polycarbonate oligomers such as oligomers comprising hydroquinone, bisphenol-A, 3-(4-hydroxyphenyl)-1,1,3-trimethylindan-5-ol; 1-(4-hydroxyphenyl)-1,3,3-trimethylindan-5-ol; 4,4'-(3,3,5-trimethylcyclohexylidene)diphenol, 1,1-bis(4-hydroxy-3-methylphenyl)cyclohexane, or the like; and bishaloformates of glycols including, but not limited to, bishaloformates of ethylene glycol, neopentyl glycol, and polyethylene glycol. Mixtures of haloformates may be employed. In a particular embodiment carbonyl chloride, also known as phosgene, is employed. In another particular embodiment diphenylcarbonate is employed.

Conditions for preparing polycarbonates include, but are not limited to, solution processes, interfacial processes, melt processes, transesterification processes, solid-state processes, and redistribution processes, and combinations thereof. Certain of these processes often employ phosgene as carbonate precursor. Solution processes may comprise a stoichiometric amount of base such as triethylamine or pyridine. If an interfacial process is used, the addition of various phase transfer catalysts is optional. Phase transfer catalysts which are suitable include, but are not limited, to tertiary amines, such as triethylamine, ammonium salts, such as tetrabutylammonium bromide; or hexaethylguanidinium chloride.

In one embodiment the polycarbonates are prepared by a melt transesterification process. This process does not require the use of phosgene or a solvent, and often minimizes the formation of low molecular weight contaminants, such as cyclic and linear low molecular weight oligomers in the final polymer. In an illustrative example polycarbonate monomers are mixed with a carbonate source, such as a diarylcarbonate, and a small amount of catalyst, such as an alkali metal hydroxide or quaternary ammonium hydroxide or mixture thereof, and heated under a vacuum according to a protocol in which the temperature is raised through a series of stages while the pressure in the headspace over the reaction mixture is lowered from ambient pressure to about 1 Torr. The time of the stages and the temperature are such that mechanical losses of material through foaming and the like are avoided. In some embodiments the diarylcarbonate is diphenylcarbonate, and phenol and excess diphenylcarbonate may be removed overhead to complete the polymerization process. At least one of optional end-capping agents, coupling agents, or branching agents which are well-known in the art or which are disclosed in the present invention may be included in the reaction if desired. The product high polymer may then be isolated as a melt which may be compounded with other additives, such as stabilizers and mold release agents prior to pelletization. Suitable carbonate sources, catalysts and reaction conditions may be found, for example, in U.S. Pat. No. 5,880,248, and *Kirk-Othmer Encyclopedia of Chemical Technology*, Fourth Edition, Volume 19, pp. 584-600, herein incorporated by reference.

In various embodiments polycarbonates of the invention have a weight average molecular weight in a range of between about 5,000 and about 100,000, in other embodiments a weight average molecular weight in a range of between about 10,000 and about 65,000, and in still other embodiments a weight average molecular weight in a range of between about 18,000 and about 55,000 as measured by gel permeation chromatography versus polystyrene standards. In other embodiments polycarbonates of the invention have a weight average molecular weight in a range of between about 30,000 and about 55,000, as measured by gel permeation chromatography versus polystyrene standards.

In one embodiment of the invention essentially all the polymer chains of a triazine-comprising polymer have at least one nucleophilic group attached thereto. In one embodiment essentially all the polymer chains have at least one nucleophilic end-group. In another embodiment of the invention only a portion of polymer chains have at least one nucleophilic group attached thereto. In another embodiment only a portion of polymer chains have at least one nucleophilic end-group. In one embodiment of the invention essentially all the polymer nucleophilic groups (for example, nucleophilic end-groups) are capped through reaction with at least one triazine-comprising capping agent. In some embodiments essentially all the polymer chains have a triazine-comprising structural unit attached to at least two terminal sites on the polymer. In another embodiment of the invention only a portion of polymer nucleophilic groups (for example, nucleophilic end-groups) are capped through reaction with at least one triazine-comprising capping agent. In other embodiments only a portion of the polymer chains have a triazine-comprising structural unit attached to at least two terminal sites on the polymer. In some embodiments a triazine-comprising capping agent may be employed in combination with at least one other non-triazine capping agent for reaction with monomer or polymer nucleophilic groups, particularly nucleophilic end-groups.

Depending upon what other functionality may be present on the triazine-comprising capping agent and other factors such as reaction conditions and type of nucleophilic group on a polymer or monomer, those skilled in the art will realize that there may be circumstances in which a triazine-comprising capping agent designed to be monofunctional (that is, containing one L group) may react with a nucleophilic group to some minor extent at more than one site on the triazine ring, it being only necessary that the triazine substituent Z react with a nucleophilic group on a polymer or monomer at a slower rate than the leaving group L. Similarly a triazine-comprising capping agent designed to be difunctional (that is, containing two L groups) may react with a nucleophilic group to some minor extent at more than two sites on the triazine ring, it being only necessary that the triazine substituent Z react with a nucleophilic group on a polymer or monomer at a slower rate than the leaving group L. It is often the case that substituents, such as aryloxy, on a triazine ring become increasingly resistant to reaction, such as displacement or exchange, when they are sterically hindered. In an illustrative example a 2,6-disubstituted aryloxy moiety is often more resistant to reaction with a nucleophilic group than its corresponding mono-substituted aryloxy or unsubstituted aryloxy analog.

In various embodiments of the present invention polymers may comprise a triazine-comprising moiety as a terminal unit, or as a structural unit in the polymer chain other than at a terminal site, or both types of structural units. In the latter embodiment the mixture of types of structural units may be derived from reaction of nucleophile-containing polymer or monomer with either one or more than one type of triazine-comprising capping agent, for example a mixture of a monofunctional triazine-comprising capping agent and a difunctional triazine-comprising capping agent.

Difunctional triazine-comprising capping agents may be employed to chain-extend nucleophile-terminated polymers through reaction with terminal nucleophilic groups on more than one polymer chain. In such embodiments the number average molecular weight of the triazine-comprising polymer typically increases, and in one embodiment the increase is at least 500 Daltons, in another embodiment at least 1000 Daltons, in still another embodiment at least 2000 Daltons, and in still another embodiment at least 2500 Daltons. In other examples of such embodiments the intrinsic viscosity of the triazine-comprising polymer typically increases, and in one embodiment the increase is at least 0.05 IV units, in another embodiment at least 0.1 IV units, and in still another embodiment at least 0.2 IV units. IV units are usually deciliters per gram.

Trifunctional triazine-comprising capping agents may be employed to branch nucleophile-terminated polymers through reaction with terminal nucleophilic groups on more than one polymer chain. In such embodiments the value for at least one viscosity value typically changes. In particular melt viscosity (as measured by DIN 54811) increases, or melt flow rate (as measured by ISO 1133) decreases, or melt volume rate (as measured by ISO 1133) decreases for the triazine-comprising polymer, and in one embodiment the change is at least 5%, in another embodiment at least 10%, in still another embodiment at least 15%, in still another embodiment at least 20%, and in still another embodiment at least 50% compared to the polymer initial value.

Those skilled in the art will recognize that whether a difunctional or trifunctional triazine-comprising capping agent reacts with nucleophilic groups on more than one polymer chain may be at least partially dependent upon the stoichiometric amount of capping agent added. For example, use of a stoichiometric excess of difunctional triazine-comprising capping agent may result in some portion of polymer chains being only end-capped with triazine moiety in addition to polymers chains being chain-extended. In one embodiment a substantial portion up to and including essentially all chains containing terminal nucleophilic groups may be simply end-capped if a large stoichiometric excess of difunctional triazine-comprising capping agent in used. In another example, use of a stoichiometric excess of trifunctional triazine-comprising capping agent may result in a some portion of polymer chains being only chain-extended or end-capped with triazine moiety in addition to polymers chains being branched. In one embodiment the present invention encompasses both the product thereof and the process of using a difunctional triazine-comprising capping agent to provide a polymer comprising a mixture of end-capped and chain-extended chains. In other embodiments the present invention also encompasses both the product thereof and the process of using a trifunctional triazine-comprising capping agent to provide a polymer comprising a mixture of chain-extended and branched chains or a mixture of end-capped, chain-extended, and branched chains.

In another embodiment polymers with nucleophilic groups capped through reaction with a triazine-comprising capping agent may be used as polymerization promoters for growing a polymer chain from at least one point of the capped polymer. In one embodiment polymers with nucleophilic groups end-capped through reaction with a di- or trifunctional triazine or chain-extended with a trifunctional triazine may be used as polymerization promoters for growing a polymer chain from at least one point of the capped polymer. In a particular embodiment a polycarbonate comprising at least one triazine structural unit wherein the triazine structural unit possesses at least one L group may be used in reaction with at least one dihydric phenol and carbonate precursor to grow a new polycarbonate chain attached to the initial polycarbonate chain through a triazine moiety.

Polymers or monomers comprising nucleophilic groups may be combined and reacted with triazine-comprising capping agents using any known method. Representative methods include, but are not limited to, solution methods, interfacial methods, melt methods, slurry methods, solid-state methods, and combinations thereof. Any method employed may be a batch method, semi-continuous method, or continuous method. The amount of triazine-comprising capping agent employed will generally depend upon the level of nucleophilic groups contained in a polymer or monomer, and the desired level of triazine-comprising compound to be incorporated into a final product. In one embodiment the amount of triazine-comprising capping agent employed is in a range of between about 5 mole % and about 400 mole %; in another embodiment in a range of between about 20 mole % and about 200 mole %; in another embodiment in a range of between about 40 mole % and about 150 mole %; in still another embodiment in a range of between about 60 mole % and about 120 mole % based on moles nucleophilic groups contained in the polymer or monomer.

In one embodiment of the present invention polymers or monomers comprising nucleophilic groups are reacted with triazine-comprising capping agents in the presence of at least one catalyst. Suitable catalysts comprise those known to effect transesterification reactions. In various embodiments such catalysts comprise acidic, neutral, or basic catalysts, such classifications often being based on the reaction of a conventional acid-base indicator and the catalyst when the latter is dissolved in a polar ionizing solvent such as water. In one embodiment a basic catalyst is employed. Suitable basic catalysts comprise the alkali metals, examples of which comprise lithium, sodium, potassium, rubidium, and cesium; and their corresponding carbonates, hydroxides, hydrides, borohydrides, phenates, bisphenates, (that is, salt of a bisphenol); carboxylates such as acetate or benzoate; fluorides; and oxides. Group II and III elements can also be used in place of the alkali metals of the foregoing classes of compounds such as metals and compounds of calcium, magnesium and aluminum. Other bases comprise trialkyl or triaryl tin hydroxides, acetates, phenates, and the like. In particular embodiments examples of catalysts comprise lithium, sodium, potassium, rubidium, and cesium metals; lithium hydride, aluminum tri-isopropoxide and triphenyl tin hydroxide.

In other embodiments catalysts comprise metal oxides, metal acetates, titanium, and tin compounds. Suitable metal oxides comprise antimony trioxide, germanium oxide, arsenic trioxide, lead oxide, magnesium oxide, and zinc oxide. Suitable metal acetates comprise cobalt acetate, zinc acetate, cadmium acetate and manganese acetate. Suitable titanium compounds comprise the titanates such as tetrabutyl titanate and tetraisopropyl titanate. Suitable tin compounds comprise dibutyl tin oxide, dibutyl tin methoxide and dibutyl tin dilaurate.

In other particular embodiments illustrative examples of catalysts comprise at least one nitrogen-containing basic compound, phosphorus-containing basic compound, alkali metal compound, alkaline earth metal compound, or a boric acid or boric ester. Mixtures of such catalysts may also be employed.

In various embodiments nitrogen-containing basic compounds comprise alkyl-, aryl-, or alkaryl quaternary ammonium hydroxides such as tetramethylammonium hydroxide, tetraethylammonium hydroxide, tetrabutylammonium hydroxide and trimethylbenzylammonium hydroxide; tertiary amines represented by $R_3N$ (wherein R is alkyl or aryl or a mixture thereof) such as trimethylamine, triethylamine, dimethylbenzylamine and triphenylamine; secondary amines represented by $R_2NH$ (wherein R is as defined above); primary amines represented by $RNH_2$ (wherein R is as defined above); ammonia; or basic salts such as tetramethylammonium borohydride, tetrabutylammonium borohydride, tetrabutylammonium tetraphenyl borate, tetramethylammonium tetraphenyl borate, and hexaalkylguanidinium salts and alpha,omega-bis(pentaalkylguanidinium)alkane salts, comprising hexaethylguanidinium halides, alpha,omega-bis(pentaalkylguanidinium)alkane halides, and hexaethylguanidinium chloride. In various embodiments phosphorus-containing basic compounds comprise quaternary phosphonium hydroxides and quaternary phosphonium carboxylates, such as tetrabutylphosphonium acetate.

In various embodiments alkali metal compounds comprise sodium hydroxide, potassium hydroxide, lithium hydroxide, sodium hydrogencarbonate, potassium hydrogencarbonate, lithium hydrogencarbonate, sodium carbonate, potassium carbonate, lithium carbonate, sodium acetate, potassium acetate, lithium acetate, sodium stearate, potassium stearate, lithium stearate, sodium borohydride, potassium borohydride, lithium borohydride, sodium borophenylate, sodium benzoate, potassium benzoate, lithium benzoate, disodium hydrogenphosphate, dipotassium hydrogenphosphate, dilithium hydrogenphosphate, disodium salt of bisphenol A, dipotassium salt of bisphenol A, dilithium salt of bisphenol A, sodium phenylate, potassium phenylate, and lithium phenylate.

In various embodiments alkaline earth metal compounds comprise calcium hydroxide, barium hydroxide, magnesium hydroxide, strontium hydroxide, calcium hydrogencarbonate, barium hydrogencarbonate, magnesium hydrogencarbonate, strontium hydrogencarbonate, calcium carbonate, barium carbonate, magnesium carbonate, strontium carbonate, calcium acetate, barium acetate, magnesium acetate, strontium acetate, calcium stearate, barium stearate, magnesium stearate and strontium stearate.

In various embodiments boric acid or boric acid ester compounds comprise boric acid and boric acid esters represented by the general formula $B(OR)_n(OH)_{3-n}$ (wherein R is alkyl or aryl, and n is 1, 2 or 3), and boric acid esters comprising trimethyl borate, triethyl borate, tributyl borate, trihexyl borate, triheptyl borate, triphenyl borate, tritolyl borate and trinaphthyl borate.

Catalyst may be present in one embodiment at a total level of about $10^{-8}$ moles to about 0.1 moles, in another embodiment at a total level of about $10^{-8}$ moles to about 0.06 moles, in another embodiment at a total level of about $10^{-8}$ moles to about 0.02 moles, in another embodiment at a total level of about $10^{-7}$ moles to about 0.02 moles, in another embodiment at a total level of about $10^{-6}$ moles to about 0.02 moles, in another embodiment at a total level of about $10^{-5}$ moles to about 0.02 moles, in another embodiment at a total level of about $10^{-4}$ moles to about 0.02 moles, and in still another embodiment at a total level of about $10^{-3}$ moles to about 0.02 moles, in all cases per mole of polymer repeat unit, or in the case of polycarbonates per mole of the aromatic dihydroxy compound.

In various embodiments the amount of the nitrogen containing basic compound employed is in one embodiment from about $10^{-6}$ moles to about $10^{-1}$ moles and in another embodiment from about $10^{-5}$ moles to about $10^{-2}$ moles, in all cases per mole of polymer repeat unit, or in the case of polycarbonates per mole of the aromatic dihydroxy compound. The amount of the alkali metal or alkaline earth metal compound employed is in one embodiment from about $10^{-8}$ moles to about $10^{-3}$ moles, in another embodiment from about $10^{-7}$ moles to about $10^{-4}$ moles, and in still another embodiment from about $10^{-7}$ moles to about $10^{-5}$ moles, in all cases per mole of polymer repeat unit, or in the case of polycarbonates per mole of the aromatic dihydroxy compound. The amount of the boric acid or boric acid ester is in one embodiment from about $10^{-8}$ moles to about $10^{-1}$ moles, in another embodiment from about $10^{-7}$ moles to about $10^{-2}$ moles, and in still another embodiment from about $10^{-6}$ moles to about $10^{-4}$ moles, in all cases per mole of polymer repeat unit, or in the case of polycarbonates per mole of the aromatic dihydroxy compound.

Prior to its combination with one or more reactants or its introduction into a reaction mixture, a catalyst may be in liquid form, for example in the case of solid catalysts through melting or through dissolution in a liquid or normally solid, low melting solvent. In various embodiments solvents comprise phenol and substituted phenols. Substituted phenols which can be used comprise those comprising at least one substituent R, wherein R comprises alkyl of 1 to 10 carbon atoms, alkoxy of 1 to 10 carbon atoms, aryl of 6 to 10 carbon atoms, chloro, bromo or mixtures thereof. Illustrative examples of solvents comprise o-benzyl-phenol, o-bromophenol, m-bromophenol, m-chlorophenol, p-chlorophenol, 2,4-dibromophenol, 2,6-dichlorophenol, 3,5-dimethoxyphenol, o-ethoxyphenol, m-ethyl-phenol, p-ethylphenol, o-isopropylphenol, m-methoxyphenol, m-propylphenol, p-propylphenol, and the like. In other embodiments solvents may be of the ether type, for example, tetrahydrofuran and the various glymes, for example, ethylene glycol dimethylether and the like. Liquid phosphites such as triphenyl phosphite and tris(nonylphenyl)phosphite, and phosphates such as trimethyl or triethyl phosphate are also useful in diluents. In one embodiment any solvent or diluent used with a catalyst corresponds to a leaving group compound derived from triazine-comprising capping agent. Combinations of catalysts and combinations of solvents may also be used. In various embodiments when a basic catalyst is employed, the catalyst may be introduced concurrently with the aforementioned molten reactants to the polymerization to avoid heating the reactants in the presence of the catalyst prior to onset of the transesterification.

In one embodiment combination and reaction of polymer or monomer with triazine-comprising capping agent is performed in any type of melt-processing equipment, illustrative examples of which include a melt mixer and an extruder. In another embodiment, when a polymer is liquid or low viscosity at room temperature, combination of polymer or monomer with triazine-comprising capping agent may be performed in any type of mixing equipment, optionally in the presence of a solvent for either polymer or monomer, or triazine compound or both, and typically with heating. In various embodiments the order of mixing of triazine-comprising capping agent with polymer or monomer may comprise adding triazine compound to any reaction equipment before adding the polymer or monomer to be reacted, or combining triazine compound with polymer or monomer and then adding to any reaction equipment, or adding triazine compound to any reaction equipment after the polymer or monomer, for example through addition of triazine compound at a down-stream feedport of an extruder to which polymer or monomer has been fed at an initial feedport. In various embodiments addition of triazine compound to an extruder may be by liquid or melt injection or using a side-feeder. Also in various embodiments triazine-comprising capping agent may be combined with polymer or monomer as the triazine compound itself, or as a solution or slurry of triazine compound in a solvent, or as a mixture with another substance, for example as a concentrate of triazine compound in a polymer or monomer, for example the polymer for which the triazine compound is to serve as a nucleophile-capper. Any method used for reacting polymers or monomers with triazine-comprising capping agents may beneficially comprise a process step for devolatilization of leaving group compound. For example a melt mixer or an extruder or a horizontally agitated polymerization tank used for reacting polymers or monomers with triazine-comprising capping agents may comprise a devolatilization step. In the case of an extruder a devolatilization step may comprise applying reduced pressure at one or more extruder barrel segment downstream of any extruder reaction zone. If desired, leaving group compound may be recovered and recycled using known methods. In one embodiment leaving group compound is recycled for use in reaction to make triazine-comprising capping agent. In one embodiment in an extrusion process subsequent feedports or further molding and extrusion processes may be used to add commonly known additives such as, for example, antioxidants, antistatic agents, inert fillers, ultraviolet radiation absorbers and stabilizers, hydrolytic stabilizers, impact modifiers, mold release agents, color stabilizers, flame retardants, and the like. Whatever process is used, a nucleophile-capped polymer is isolated using standard methods including, if desired, converting the polymer into pellets. In one embodiment polymers comprising nucleophilic groups are reacted with triazine-comprising capping agents in a melt process in which a processing aid has been adding to the mixture. Examples of processing aids include known plasticizers and also miscible polymers, such as polystyrene which is miscible with poly(phenylene ether)s.

In a particular embodiment a triazine-comprising capping agent may be combined with a polycarbonate or polycarbonate monomers at some stage of a melt polycarbonate synthesis. In a particular embodiment a triazine-comprising capping agent may be employed in a manner such as to allow polycarbonate polymerization to be carried out rapidly at close to stoichiometric conditions until a desired molecular weight is achieved and then to allow rapid increase in the endcap level and/or molecular weight of the polycarbonate to a desired level by adding the endcapping agent. Polycarbonates endcapped with triazine-comprising moieties often have beneficial properties such as at least one of improved impact strength, improved melt flow rate, improved optical properties, and improved adhesion to metal.

In various embodiments the triazine-comprising polymers of the present invention may further comprise additives known in the art, which may be added by any known method. Illustrative additives include, but are not limited to, pigments, dyes, impact modifiers, UV screeners, radiation screeners, flame retardants, fillers, heat stabilizers, color stabilizers, flow aids, ester interchange inhibitors, antistatic agents, hydrolytic stability improvers, chemical resistance improvers, dimensional stability improvers, weatherability improvers, gloss improvers, water repellents, anti-staining aids, metal flakes, adhesion promoters, and mold release agents.

Articles comprising a polymer comprising triazine structural units are another embodiment of the present invention. In various embodiments articles may consist essentially of polymers comprising triazine structural units or, if desired, said polymers in admixture with polymer additives known in the art.

In one embodiment articles are prepared from polycarbonates comprising triazine structural units. Such articles may possess advantageous properties such as low water absorption, good processability and low birefringence, and they can be advantageously utilized to produce optical articles. End-use applications for optical articles include, but are not limited to, a digital audio disk, a digital versatile disk, an optical memory disk, a compact disk, an ASMO device and the like; optical lenses, such as contact lenses, lenses for glasses, lenses for telescopes, and prisms; optical fibers; magneto optical disks; information recording media; information transferring media; disks for video cameras, disks for still cameras and the like.

In other embodiments articles of the present invention are multilayer articles comprising two or more layers, typically in contiguous superposed contact with one another. In various embodiments multilayer articles comprise a substrate layer comprising at least one thermoplastic polymer, thermoset polymer, cellulosic material, glass, ceramic, or metal, and at least one coating layer thereon, said coating layer comprising a triazine-comprising polymer, particularly a polycarbonate comprising triazine structural units. Optionally, the multilayer articles may further comprise an interlayer, for example an adhesive interlayer (or tie layer), between any substrate layer and any coating layer comprising a triazine-comprising polymer. Multilayer articles of the invention include, but are not limited to, those which comprise a substrate layer and a coating layer comprising a triazine-comprising polymer; those which comprise a substrate layer with a coating layer comprising said polymer on each side of said substrate layer; and those which comprise a substrate layer and at least one coating layer comprising a triazine-comprising polymer with at least one interlayer between a substrate layer and a coating layer. Any interlayer may be transparent and/or may contain an additive, for example a colorant or decorative material such as metal flake. If desired, an overlayer may be included over the coating layer comprising a triazine-comprising polymer, for example to provide abrasion or scratch resistance. In one embodiment the substrate layer, coating layer comprising a triazine-comprising polymer, and any interlayers or overcoating layers are in contiguous superposed contact with one another. In any embodiment a triazine-comprising polymer layer may comprise conventional additives known in the art for use with polymers, including conventional UV screeners, heat stabilizers, flow promoters, lubricants, dyes, pigments, and the like. In one embodiment a triazine comprising polymer is a polycarbonate, for example a bisphenol A polycarbonate.

Representative articles which can be made which comprise compositions of the invention include aircraft, automotive, truck, military vehicle (including automotive, aircraft, and water-borne vehicles), and motorcycle exterior and interior components, including panels, quarter panels, rocker panels, trim, fenders, doors, decklids, trunklids, hoods, bonnets, roofs, bumpers, fascia, grilles, mirror housings, pillar appliques, cladding, body side moldings, wheel covers, hubcaps, door handles, spoilers, window frames, headlamp bezels, headlamps, tail lamps, tail lamp housings, tail lamp bezels, license plate enclosures, roof racks, and running boards;

enclosures, housings, panels, and parts for outdoor vehicles and devices; enclosures for electrical and telecommunication devices; outdoor furniture; boats and marine equipment, including trim, enclosures, and housings; outboard motor housings; depth finder housings, personal water-craft; jet-skis; pools; spas; hot-tubs; steps; step coverings; building and construction applications such as glazing, roofs, windows, floors, decorative window furnishings or treatments; treated glass covers for pictures, paintings, posters, and like display items; optical lenses; ophthalmic lenses; corrective ophthalmic lenses; implantable ophthalmic lenses; wall panels, and doors; protected graphics; outdoor and indoor signs; enclosures, housings, panels, and parts for automatic teller machines (ATM); enclosures, housings, panels, and parts for lawn and garden tractors, lawn mowers, and tools, including lawn and garden tools; window and door trim; sports equipment and toys; enclosures, housings, panels, and parts for snowmobiles; recreational vehicle panels and components; playground equipment; articles made from plastic-wood combinations; golf course markers; utility pit covers; computer housings; desk-top computer housings; portable computer housings; lap-top computer housings; palm-held computer housings; monitor housings; printer housings; keyboards; FAX machine housings; copier housings; telephone housings; mobile phone housings; radio sender housings; radio receiver housings; light fixtures; lighting appliances; network interface device housings; transformer housings; air conditioner housings; cladding or seating for public transportation; cladding or seating for trains, subways, or buses; meter housings; antenna housings; cladding for satellite dishes; coated helmets and personal protective equipment; coated synthetic or natural textiles; coated photographic film and photographic prints; coated painted articles; coated dyed articles; coated fluorescent articles; coated foam articles; and like applications. The invention further contemplates additional fabrication operations on said articles, such as, but not limited to, molding, in-mold decoration, baking in a paint oven, lamination, and/or thermoforming.

Without further elaboration, it is believed that one skilled in the art can, using the description herein, utilize the present invention to its fullest extent. The following examples are included to provide additional guidance to those skilled in the art in practicing the claimed invention. While some of the examples are illustrative of various embodiments of the claimed invention, others are comparative. The examples provided are merely representative of the work that contributes to the teaching of the present application. Accordingly, these examples are not intended to limit the invention, as defined in the appended claims, in any manner.

The following examples illustrate syntheses of triazine-comprising compounds.

EXAMPLE 1

Synthesis of 2-chloro-4,6-bis(2,6-dimethylphenoxy)-1,3,5-triazine: A solution of 27.7 grams (g) (0.15 moles) cyanuric chloride, 36.6 g (0.30 moles) 2,6-xylenol and 0.97 g (0.003 moles) tetra-n-butylammonium chloride in 250 milliliters (ml) of to toluene was chilled in an ice-water bath. To the stirred solution was slowly added a solution of sodium hydroxide, 12.0 g (0.3 moles) in 25 ml of water. The mixture was maintained at a temperature below about 20° C. for two hours and then stirred at room temperature for an additional 16 hours. The resulting mixture was filtered. The collected solids were washed with water. The combined filtrate and washes were transferred to a separatory funnel and the aqueous phase was discarded. The organic phase was washed sequentially with equal portions of 10% aqueous hydrochloric acid, water and saturated sodium chloride solution. Evaporation of the organic phase afforded an off-white solid which was combined with the solids from the filtration of the reaction mixture. Recrystallization of these solids from a mixture of toluene and hexane afforded pure 2-chloro-4,6-bis(2,6-dimethylphenoxy)-1,3,5-triazine, melting point 161-162° C.

EXAMPLE 2

Synthesis of 2-(2-carbomethoxyphenoxy)-4,6-bis(2,6-dimethylphenoxy)-1,3,5-triazine: A 250 ml 3-neck flask equipped with a condenser, a nitrogen inlet, a magnetic stirrer and an addition funnel was charged with sodium hydride (3.0 g of a 60% dispersion in oil; 0.075 moles). The dispersion was rinsed twice with hexane followed by decantation. The flask was then charged with 60 ml of dry N-methyl-2-pyrrolidinone (NMP) and methyl salicylate, 11.4 g (0.075 moles). The resulting mixture was stirred until no further hydrogen evolution was noted. To this mixture was added dropwise, a solution of 2-chloro-4,6-bis(2,6-dimethylphenoxy)-1,3,5-triazine (25 g; 0.07 moles) in a minimal amount of dry NMP. This mixture was heated at 60° C. for three hours at which point liquid chromatographic analysis indicated that no more of the triazine starting material was present. The solution was poured into 200 ml of ice-water containing a little hydrochloric acid. The resulting slurry was extracted three times with 150 ml portions of dichloromethane. Combined extracts were washed sequentially with equal portions of 10% aqueous hydrochloric acid, 5% aqueous sodium hydroxide, water and brine. Evaporation of the organic phase afforded an oil which solidified to a foam by drying in a cooling bath under to high vacuum. The foam fused to a glass at 50° C. and the glass liquefied at between 85-90° C. The proton ($^1$H) nuclear magnetic resonance (NMR) spectrum was consistent with the desired product, 2-(2-carbomethoxyphenoxy)-4,6-bis(2,6-dimethylphenoxy)-1,3,5-triazine.

EXAMPLE 3

Synthesis of 2-chloro-4,6-bis(2,4,6-tribromophenoxy)-1,3,5-triazine: The procedure of Example 1 is essentially repeated except that two equivalents of 2,4,6-tribromophenol is used in place of 2,6-xylenol. The product is the desired 2-chloro-4,6-bis(2,4,6-tribromophenoxy)-1,3,5-triazine.

EXAMPLE 4

Synthesis of 2-(2-carbomethoxyphenoxy)-4,6-bis(2,4,6-tribromophenoxy)-1,3,5-triazine: The procedure of Example 2 is essentially repeated except that 2-chloro-4,6-bis(2,4,6-tribromophenoxy)-1,3,5-triazine is used in place of 2-chloro-4,6-bis(2,6-dimethylphenoxy)-1,3,5-triazine. The product is the desired 2-(2-carbomethoxyphenoxy)-4,6-bis(2,4,6-tribromophenoxy)-1,3,5-triazine.

EXAMPLE 5

Synthesis of 2,4-bis(2-carbomethoxyphenoxy)-6-(2,4,6-trimethylphenoxy)-1,3,5-triazine: The procedure of Example 2 is essentially repeated except that one equivalent of 2,4-dichloro-6-(2,4,6-trimethylphenoxy)-1,3,5-triazine (synthesized as described in U.S. Pat. No. 5,229,513) is used along with about 2 equivalents of methyl salicylate. The product is the desired 2,4-bis(2-carbomethoxyphenoxy)-6-(2,4,6-trimethylphenoxy)-1,3,5-triazine.

EXAMPLE 6

Synthesis of 2-allyloxy-4,6-dichloro-1,3,5-triazine: A solution of 91.8 grams (g) (0.49 moles) cyanuric chloride in 400 ml of dichloromethane was treated with 28.91 g (0.49 moles) allyl alcohol, and the mixture was chilled in an ice-water bath to about 0-5° C. The ice-water bath was removed and 45.79 g 50% aqueous sodium hydroxide was added over about 30 minutes with stirring keeping the temperature between about 0° C. and about 10° C. Stirring was continued for an additional 30 minutes after which time the layers were separated and the organic layer washed two times with water, and the solution was dried over magnesium sulfate. Filtration and evaporation of the solution afforded a mobile liquid. The proton and carbon nuclear magnetic resonance (NMR) spectra were consistent with the desired product, 2-allyloxy-4,6-dichloro-1,3,5-triazine.

EXAMPLE 7

Synthesis of 2-allyloxy-4,6-bis(2-carbomethoxyphenoxy)-1,3,5-triazine: The procedure of Example 2 is essentially repeated except that one equivalent of 2-allyloxy-4,6-dichloro-1,3,5-triazine is used along with about 2 equivalents of methyl salicylate. The product is the desired 2-allyloxy-4,6-bis(2-carbomethoxyphenoxy)-1,3,5-triazine.

EXAMPLE 8

Synthesis of 2,4-dichloro-6-glycidoxy-1,3,5-triazine: A solution of 73.76 g (0.4 moles) cyanuric chloride in 360 ml of dichloromethane was chilled in an ice-water bath to about 0-5° C. and 31.85 g (0.43 moles) glycidol was added. A solution of 34.4 g 50% aqueous sodium hydroxide was added over about 30-45 minutes with stirring keeping the temperature between about 0° C. and about 10° C. Stirring was continued for an additional 3 hours after which time the layers were separated and the organic layer washed two times with water, and once with brine and the solution was dried over magnesium sulfate. Filtration and evaporation of the solution afforded a white solid, a sample of which was further purified by trituration with hexane-ethyl acetate. The proton and carbon nuclear magnetic resonance (NMR) spectra were consistent with the desired product, 2,4-dichloro-6-glycidoxy-1,3,5-triazine.

EXAMPLE 9

Synthesis of 2,4-bis(2-carbomethoxyphenoxy)-6-glycidoxy-1,3,5-triazine: The procedure of Example 2 is essentially repeated except that one equivalent of 2,4-dichloro-6-glycidoxy-1,3,5-triazine is used along with about 2 equivalents of methyl salicylate. The product is the desired 2,4-bis(2-carbomethoxyphenoxy)-6-glycidoxy-1,3,5-triazine.

EXAMPLE 10

Synthesis of 2,4-dichloro-6-(2-methoxy-2-methyl-1,3-dioxolanyl)methoxy-1,3,5-triazine: The procedure of Example 8 is essentially repeated except that one equivalent of 4-hydroxymethyl-2-methoxy-2-methyl-1,3-dioxolane is used in place of glycidol, and triethylamine and a phase transfer catalyst are both added to the reaction mixture before treatment with aqueous sodium hydroxide. The product is the desired 2,4-dichloro-6-(2-methoxy-2-methyl-1,3-dioxolanyl)methoxy-1,3,5-triazine.

EXAMPLE 11

Synthesis of 2,4-bis(2-carbomethoxyphenoxy)-6-(2-methoxy-2-methyl-1,3-dioxolanyl)methoxy-1,3,5-triazine: The procedure of Example 2 is essentially repeated except that one equivalent of 2,4-dichloro-6-(2-methoxy-2-methyl-1,3-dioxolanyl)methoxy-1,3,5-triazine is used along with about 2 equivalents of methyl salicylate. The product is the desired 2,4-bis(2-carbomethoxyphenoxy)-6-(2-methoxy-2-methyl-1,3-dioxolanyl)methoxy-1,3,5-triazine.

EXAMPLE 12

Synthesis of 2-(2-carbomethoxyphenoxy)-4-(2-methoxy-2-methyl-1,3-dioxolanyl)methoxy-6-(2,4,6-trimethylphenoxy)-1,3,5-triazine: The procedure of Example 2 is essentially repeated except that one equivalent of 2-chloro-4-(2-methoxy-2-methyl-1,3-dioxolanyl)methoxy-6-(2,4,6-trimethylphenoxy)-1,3,5-triazine is used along with about 1 equivalent of methyl salicylate. The product is the desired 2-(2-carbomethoxyphenoxy)-4-(2-methoxy-2-methyl-1,3-dioxolanyl)methoxy-6-(2,4,6-trimethylphenoxy)-1,3,5-triazine.

EXAMPLE 13

Synthesis of 2-butoxy-4-(2-carbomethoxyphenoxy)-6-glycidoxy-1,3,5-triazine: The procedure of Example 2 is essentially repeated except that one equivalent of 2-butoxy-4-chloro-6-(2,4,6-trimethylphenoxy)-1,3,5-triazine (synthesized as described in U.S. Pat. No. 4,895,945) is used along with about 1 equivalent of methyl salicylate. The product is the desired 2-butoxy-4-(2-carbomethoxyphenoxy)-6-glycidoxy-1,3,5-triazine.

EXAMPLE 14

Synthesis of 2-(2-carbomethoxyphenoxy)-4,6-diglycidoxy-1,3,5-triazine: The procedure of Example 2 is essentially repeated except that one equivalent of 2-chloro-4,6-diglycidoxy-1,3,5-triazine (synthesized as described in U.S. Pat. No. 4,895,945) is used along with about 1 equivalent of methyl salicylate. The product is the desired 2-(2-carbomethoxyphenoxy)-4,6-diglycidoxy-1,3,5-triazine.

EXAMPLE 15

Synthesis of 2-(2-carbomethoxyphenoxy)-4-glycidoxy-6-(2,4,6-trimethylphenoxy)-1,3,5-triazine: The procedure of Example 2 is essentially repeated except that one equivalent of 2-chloro-4-glycidoxy-6-(2,4,6-trimethylphenoxy)-1,3,5-triazine is used along with about 1 equivalent of methyl salicylate. The product is the desired 2-(2-carbomethoxyphenoxy)-4-glycidoxy-6-(2,4,6-trimethylphenoxy)-1,3,5-triazine.

EXAMPLE 16

Synthesis of 2-chloro-4-(4-ethenylphenoxy)-6-(2,4,6-trimethylphenoxy)-1,3,5-triazine: A solution of 25.57 g (0.09 moles) 2,4-dichloro-6-(2,4,6-trimethylphenoxy)-1,3,5-triazine in 300 ml of dichloromethane was treated with 11.8 g (0.098 moles) p-hydroxystyrene (prepared by hydrolysis of p-acetoxystyrene) dissolved in about 40 ml dichloromethane. The mixture was cooled in an ice-water bath and 36.8 g of 10% aqueous sodium hydroxide solution was added with stirring over about 5 minutes. Stirring was continued for 30 minutes after which time the ice-water bath was removed and stirring was continued for about 2 hours. The mixture was treated with brine, the layers were separated, and after standing, the organic layer was washed twice with brine, and once with water, and dried over magnesium sulfate. Filtration and evaporation gave a white solid with proton NMR spectrum consistent with the desired product, 2-chloro-4-(4-ethenylphenoxy)-6-(2,4,6-trimethylphenoxy)-1,3,5-triazine.

EXAMPLE 17

Synthesis of 2-(2-carbomethoxyphenoxy)-4-(4-ethenylphenoxy)-6-(2,4,6-trimethylphenoxy)-1,3,5-triazine: The procedure of Example 2 is essentially repeated except that one equivalent of 2-chloro-4-(4-ethenylphenoxy)-6-(2,4,6-trimethylphenoxy)-1,3,5-triazine is used along with about 1 equivalent of methyl salicylate. The product is the desired 2-(2-carbomethoxyphenoxy)-4-(4-ethenylphenoxy)-6-(2,4,6-trimethylphenoxy)-1,3,5-triazine.

EXAMPLE 18

Synthesis of 2,4,6-tris(2-carbomethoxyphenoxy)-1,3,5-triazine: A solution of 13.8 grams (g) (0.075 moles) cyanuric chloride in 400 ml of dichloromethane was treated with 35.7 g (0.2346 moles) methyl salicylate and 0.7 g Adogen 464, and the mixture was chilled in an ice-water bath to about 6° C. The ice-water bath was removed and 18.8 g 50% aqueous sodium hydroxide was added over 10 minutes with stirring. Stirring was continued for about 16 hours after which time the layers were separated and the organic layer washed four times with 2% aqueous sodium hydroxide, twice with water, once with brine, and the solution was dried over magnesium sulfate. Filtration and evaporation of the solution afforded an off-white solid with melting point about 58-63° C. The proton and carbon nuclear magnetic resonance (NMR) spectra were consistent with the desired product, 2,4,6-tris(2-carbomethoxyphenoxy)-1,3,5-triazine.

The following examples illustrate syntheses of polymers comprising triazine-comprising structural units. The properties of polycarbonates were measured as follows. Weight average molecular weights (Mw) and number average molecular weights (Mn) were measured by gel permeation chromatography (GPC) versus polystyrene standards using polymer solutions at a concentration of 1 milligram per ml in dichloromethane. Free hydroxy end-group concentration (sometimes referred to as free-OH content) was measured by UV/Visible analysis of the complexes formed from the polymer with titanium tetrachloride in dichloromethane solution. Polycarbonate endcap levels in percent were calculated from the free OH content and Mn values using the equation $$\% EC = 100 - \frac{M_n(PC) \cdot W_{free\ OH}}{2 \cdot 17 \cdot 10{,}000}$$

wherein $W_{free\ OH}$ is the concentration of free OH groups in ppm.

EXAMPLE 19

A BPA polycarbonate prepared by a melt process was endcapped using an activated triazine. The BPA polycarbonate initially had Mw 18,300, Mn 7,520, free-OH content of 670 parts per million (ppm), and an endcap level of 84.6%. A batch reactor tube was charged with 25 g of BPA polycarbonate and 0.511 g ($1.084 \times 10^{-3}$ moles) 2-(2-carbomethoxyphenoxy)-4,6-bis(2,6-dimethylphenoxy)-1,3,5-triazine under nitrogen. The mixture was heated to a temperature of 300° C. and stirred for 20 minutes. After the melt mixing stage, vacuum was applied to the system to a pressure of about 50 pascals. Under these conditions the reaction was continued for 20 minutes. After the reaction stage, the polymer was removed from the reaction tube and purified by reprecipitation. The endcap level of the polycarbonate increased from 84.6% to 92.4% and the free-OH content decreased from 670 to 290 ppm. The amount of triazine endcap incorporated into the capped polymer was calculated to be 0.64 mole % (or 1.1 mass %) based on moles BPA and determined by integration of the 2.05 ppm (s, 12H, ArCH$_3$) peak in the $^1$H NMR (CDCl$_3$) spectrum of the purified polymer product. The results are shown in Table 1.

EXAMPLE 20

A batch reactor tube was charged with 25 g of BPA polycarbonate and 1.250 g ($2.651 \times 10^{-3}$ moles) 2-(2-carbomethoxyphenoxy)-4,6-bis(2,6-dimethylphenoxy)-1,3,5-triazine under nitrogen. To the reactor tube 100 microliters of an aqueous sodium hydroxide catalyst solution ($4.67 \times 10^{-3}$ molar concentration) was added. The mixture was heated to a temperature of 300° C. and stirred for 20 minutes. After the melt mixing stage, vacuum was applied to the system to a pressure of about 50 pascals. At those conditions the reaction was continued for 60 minutes. After the reaction stage the polymer was sampled from the reaction tube. The endcap level of the sampled polycarbonate increased from 84.6% to 99.1% and the Free-OH content decreased from 670 to 39 ppm. The results are shown in Table 1.

COMPARATIVE EXAMPLE 21

Example 19 was repeated except that no endcapper was charged to the reactor tube. The results are shown in Table 1.

COMPARATIVE EXAMPLE 22

Example 19 was repeated except that, instead of using 2-(2-carbomethoxyphenoxy)-4,6-bis(2,6-dimethylphenoxy)-1,3,5-triazine 0.2322 g ($1.084 \times 10^{-3}$ moles), DPC was charged to the reactor tube. The results are shown in Table 1.

COMPARATIVE EXAMPLE 23

Example 19 was repeated except that, instead of using 2-(2-carbomethoxyphenoxy)-4,6-bis(2,6-dimethylphenoxy)-1,3,5-triazine, 0.2951 g ($1.084 \times 10^{-3}$ moles) methyl salicylate phenyl carbonate was charged to the reactor tube. The results are shown in Table 1.

TABLE 1

| Example | Amt. Endcapper (moles × 10⁻³) | Added NaOH | Reaction time (minutes) | Mw | Mn | Free OH content (ppm) | Endcap level % |
|---|---|---|---|---|---|---|---|
| 19 | 1.084 | No | 20 | 18287 | 8956 | 290 | 92.4 |
| 20 | 2.651 | Yes | 60 | 16089 | 8134 | 39 | 99.1 |
| C 21 | — | No | 20 | 20992 | 11740 | 432 | 85.1 |
| C 22 | 1.084 | No | 20 | 21058 | 11692 | 347 | 88.1 |
| C 23 | 1.084 | No | 20 | 19631 | 10623 | 312 | 90.2 |

EXAMPLE 24

The process of Example 19 is essentially repeated except that 2-(2-carbomethoxyphenoxy)-4-glycidoxy-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polycarbonate comprises 4-glycidoxy-6-(2,4,6-trimethylphenoxy)-1,3,5-triazine end-groups.

EXAMPLE 25

The process of Example 19 is essentially repeated except that 2-(2-carbomethoxyphenoxy)-4-(2-methoxy-2-methyl-1,3-dioxolanyl)methoxy-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polycarbonate comprises 4-(2-methoxy-2-methyl-1,3-dioxolanyl)methoxy-6-(2,4,6-trimethylphenoxy)-1,3,5-triazine end-groups.

EXAMPLE 26

The process of Example 19 is essentially repeated except that 2-allyloxy-4,6-bis(2-carbomethoxyphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polycarbonate comprises 2-allyloxy-1,3,5-triazine structural units.

EXAMPLE 27

The process of Example 19 is essentially repeated except that 2,4,6-tris(2-carbomethoxyphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polycarbonate comprises 1,3,5-triazine structural units.

EXAMPLE 28

The process of Example 19 is essentially repeated except that 2-(2-carbomethoxyphenoxy)-4-(4-ethenylphenoxy)-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polycarbonate comprises 4-(4-ethenylphenoxy)-6-(2,4,6-trimethylphenoxy)-1,3,5-triazine end-groups.

EXAMPLE 29

A poly(2,6-dimethyl-1,4-phenylene ether) containing at least a portion of chains containing at least one hydroxy end-group is combined in the melt with 2-(2-carbomethoxyphenoxy)-4,6-bis(2,6-dimethylphenoxy)-1,3,5-triazine. The mixture is mixed and heated, and the pressure is decreased to remove at least a portion of methyl salicylate. The product is isolated including, if desired, conversion into pellets. The polymer comprises 4,6-bis(2,6-dimethylphenoxy)-1,3,5-triazine end-groups.

EXAMPLE 30

The process of Example 29 is essentially repeated except that 2-(2-carbomethoxyphenoxy)-4-glycidoxy-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polymer comprises 4-glycidoxy-6-(2,4,6-trimethylphenoxy)-1,3,5-triazine end-groups.

EXAMPLE 31

The process of Example 29 is essentially repeated except that 2-(2-carbomethoxyphenoxy)-4-(2-methoxy-2-methyl-1,3-dioxolanyl)methoxy-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polymer comprises 4-(2-methoxy-2-methyl-1,3-dioxolanyl)methoxy-6-(2,4,6-trimethylphenoxy)-1,3,5-triazine end-groups.

EXAMPLE 32

The process of Example 29 is essentially repeated except that 2-(2-carbomethoxyphenoxy)-4-(4-ethenylphenoxy)-6-(2,4,6-trimethylphenoxy)-1,3,5-triazine is used in place of 2-(2-carbomethoxyphenoxy)-4,6-bis(2,6-dimethylphenoxy)-1,3,5-triazine. Following isolation including, if desired, conversion into pellets, the polymer comprises 4-(4-ethenylphenoxy)-6-(2,4,6-trimethylphenoxy)-1,3,5-triazine end-groups.

EXAMPLE 33

A poly(2,6-dimethyl-1,4-phenylene ether) containing at least a portion of chains containing at least one hydroxy end-group and having an IV less than about 0.25 is combined in toluene solution with 2-allyloxy-4,6-bis(2-carbomethoxyphenoxy)-1,3,5-triazine. The mixture is subjected to process steps comprising mixing and heating. The product is isolated using known methods. The polymer comprises 2-allyloxy-1,3,5-triazine structural units.

EXAMPLE 34

The process of Example 33 is essentially repeated except that 2,4,6-tris(2-carbomethoxyphenoxy)-1,3,5-triazine is used in place of 2-allyloxy-4,6-bis(2-carbomethoxyphenoxy)-1,3,5-triazine, The mixture is subjected to process steps comprising mixing and heating. The product is isolated using known methods. The polymer comprises 1,3,5-triazine structural units.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims. All U.S. Patents and European Patent Applications cited herein are incorporated herein by reference.

What is claimed is:

1. A process for capping nucleophilic groups in a polycarbonate which comprises combining and reacting the polymer with a triazine-comprising capping agent of formula (I):

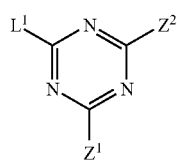

(I)

wherein $L^1$ is an aryloxy group comprising at least one electron withdrawing group ortho, meta, or para to the linkage between the aryloxy group and the triazine ring, and $Z^1$ and $Z^2$ are each independently groups which are essentially inert to reaction with a nucleophilic group on a polymer or monomer, or which react with a nucleophilic group on a polymer or monomer at a slower rate than the group, $L^1$, and wherein the resulting capped polycarbonate does not comprise a triazine-containing moiety as a structural unit in the polymer chain other than at a terminal site.

2. The process of claim 1 wherein $L^1$ is o-carbomethoxyphenoxy, and $Z^1$ and $Z^2$ are the same and are each selected from the group consisting of alkyl, aryl, alkaryl, aralkyl, alkoxy, alkylamino, arylamino, aryloxy, methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, substituted aryloxy, arylaryloxy, arylphenoxy, alkylphenoxy, 2-alkylphenoxy, 3-alkylphenoxy, 4-alkylphenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, phenylphenoxy, naphthylphenoxy, 4-cumylphenoxy, 4-(1,1,3,3-tetramethylbutyl)phenoxy, octylphenoxy, 4-tert-octylphenoxy, nonylphenoxy, dodecylphenoxy, octadecylphenoxy, pentadecylphenoxy, pentadecenylphenoxy, methoxyphenoxy, phenoxyphenoxy, benzyloxyphenoxy, n-hexyloxyphenoxy, 2-methoxyethylphenoxy, 4-(4'-oxyphenyl)-2,2,4-trimethylchroman, 2-(4'-oxyphenyl)-2,4,4-trimethylchroman, 1-(1-methyl-1-phenylethyl)-4-(1-methyl-1-(4'-oxyphenyl)ethyl)-benzene, 1,3-bis(1-methyl-1-phenylethyl)-5-(1-methyl-1-(4'-oxyphenyl)ethyl)-benzene, 4-cyanophenoxy, dialkylphenoxy, 2,6-dialkylphenoxy, 2,6-dimethylphenoxy, 2,6-di-t-butylphenoxy, 2,4-dialkylphenoxy, 2,4-di-t-butylphenoxy, 2,5-dialkylphenoxy, 2,5-di-t-butylphenoxy, 2,5-dicumylphenoxy, 3,5-dialkylphenoxy, 3,5-di-t-butylphenoxy, 3,5-dicumylphenoxy, 2,3-dialkylphenoxy, 2,3-di-t-butylphenoxy, dimethoxyphenoxy, halophenoxy, 4-halophenoxy, 4-bromophenoxy, dihalophenoxy, dibromophenoxy, 2,6-dihalophenoxy, 2,6-dibromophenoxy, 2,6-dichlorophenoxy, 2,6-(dialkoxycarbonyl)phenoxy, 2,6-(dimethoxycarbonyl)phenoxy, trialkylphenoxy, 2,3,6-trialkylphenoxy, 2,3,6-trimethylphenoxy, 2,4,6-trialkylphenoxy, 2,4,6-trimethylphenoxy, trihalophenoxy, tribromophenoxy, 2,4,6-trihalophenoxy, 2,4,6-tribromophenoxy, and 2,4,6-trichlorophenoxy.

3. The process of claim 1 wherein either $Z^1$, or $Z^2$, or both $Z^1$ and $Z^2$ are selected from the group consisting of vinyl, allyl, propargyloxy, olefinic groups of formula (VII; $Fu^1$), epoxy groups of formula (VIII; $Fu^2$), and cyclic orthoester groups of formula (IX; $Fu^3$):

(VII)

(VIII)

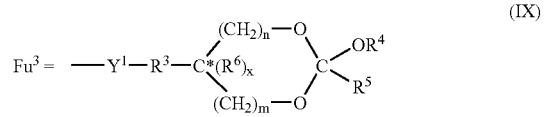

(IX)

wherein $R^1$ is an alkylene or arylene radical; $R^2$ is hydrogen, alkyl, or aryl; $Y^1$ is nitrogen or oxygen; $R^3$ is a $C_{1-6}$ alkylene radical, and $R^4$ is a $C_{1-4}$ primary or secondary alkyl radical or is an alkylene radical forming a second 5- or 6-membered ring with $C^*$, $R^5$ is a $C_{1-4}$ primary or secondary alkyl or $C_{6-10}$ aromatic radical, or $R^4$ and $R^5$ together with the atoms connecting them form a 5-, 6-, or 7-membered ring; $R^6$ is hydrogen or a $C_{1-4}$ primary or secondary alkyl; m is zero or one, and n is from 1 to 2 m; and x is zero when $R^4$ and $C^*$ form a ring and is otherwise one.

4. The process of claim 3 wherein $L^1$ is o-carbomethoxyphenoxy; $Z^1$ is selected from the group consisting of alkyl, aryl, alkaryl, aralkyl, alkoxy, alkylamino, arylamino, aryloxy, methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, substituted aryloxy, arylaryloxy, arylphenoxy, alkylphenoxy, 2-alkylphenoxy, 3-alkylphenoxy, 4-alkylphenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, phenylphenoxy, naphthylphenoxy, 4-cumylphenoxy, 4-(1,1,3,3-tetramethylbutyl)phenoxy, octylphenoxy, 4-tert-octylphenoxy, nonylphenoxy, dodecylphenoxy, octadecylphenoxy, pentadecylphenoxy, pentadecenylphenoxy, methoxyphenoxy, phenoxyphenoxy, benzyloxyphenoxy, n-hexyloxyphenoxy, 2-methoxyethylphenoxy, 4-(4'-oxyphenyl)-2,2,4-trimethylchroman, 2-(4'-oxyphenyl)-2,4,4-trimethylchroman, 1-(1-methyl-1-phenylethyl)-4-(1-methyl-1-(4'-oxyphenyl)ethyl)-benzene, 1,3-bis(1-methyl-1-phenylethyl)-5-(1-methyl-1-(4'-oxyphenyl)ethyl)-benzene, 4-cyanophenoxy, dialkylphenoxy, 2,6-dialkylphenoxy, 2,6-dimethylphenoxy, 2,6-di-t-butylphenoxy, 2,4-dialkylphenoxy, 2,4-di-t-butylphenoxy, 2,5-dialkylphenoxy, 2,5-di-t-butylphenoxy, 2,5-dicumylphenoxy, 3,5-dialkylphenoxy, 3,5-di-t-butylphenoxy, 3,5-dicumylphenoxy, 2,3-dialkylphenoxy, 2,3-di-t-butylphenoxy, dimethoxyphenoxy, halophenoxy, 4-halophenoxy, 4-bromophenoxy, dihalophenoxy, dibromophenoxy, 2,6-dihalophenoxy, 2,6-dibromophenoxy, 2,6-dichlorophenoxy, 2,6-(dialkoxycarbonyl)phenoxy, 2,6-(dimethoxycarbonyl)phenoxy, trialkylphenoxy, 2,3,6-trialkylphenoxy, 2,3,6-trimethylphenoxy, 2,4,6-trialkylphenoxy, 2,4,6-trimethylphenoxy, trihalophenoxy, tribromophenoxy, 2,4,6-trihalophenoxy, 2,4,6-tribromophenoxy, and 2,4,6-trichlorophenoxy; and $Z^2$ is selected from the group consisting of vinyl, allyl, allyloxy, 2-allylphenoxy, 4-allylphenoxy, 4-ethenylphenoxy, cinnamyloxy, 4-allyl-2-methoxyphenoxy, propargyloxy, glycidoxy, and 4-oxymethyl-2-methoxy-2-methyl- 1,3-dioxolane.

5. The process of claim 3 wherein $L^1$ is o-carbomethoxyphenoxy; and $Z^1$ and $Z^2$ are the same and are selected from the group consisting of vinyl, allyl, allyloxy, 2-allylphenoxy, 4-allylphenoxy, 4-ethenylphenoxy, cinnamyloxy, 4-allyl-2-methoxyphenoxy, propargyloxy, glycidoxy, and 4-oxymethyl-2-methoxy-2-methyl- 1,3-dioxolane.

6. A process for capping terminal hydroxy groups in a polycarbonate which comprises combining and reacting the polymer with a triazine-comprising capping agent of the formula (I):

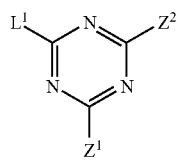

(I)

wherein $L^1$ is o-carbomethoxyphenoxy, and $Z^1$ and $Z^2$ are each independently selected from the group consisting of alkyl, aryl, alkaryl, aralkyl, alkoxy, alkylamino, arylamino, aryloxy, methyl, phenyl, methoxy, ethoxy, isopropoxy, n-butoxy, iso-butoxy, t-butoxy, benzyloxy, cyclohexyloxy, methylcyclohexyloxy, nonyloxy, decyloxy, octadecyloxy, oleyloxy, phenoxy, substituted aryloxy, arylaryloxy, arylphenoxy, alkylphenoxy, 2-alkylphenoxy, 3-alkylphenoxy, 4-alkylphenoxy, n-butylphenoxy, isobutylphenoxy, t-butylphenoxy, 4-t-butylphenoxy, n-pentylphenoxy, 4-t-amylphenoxy, n-hexylphenoxy, cyclohexylphenoxy, phenylphenoxy, naphthylphenoxy, 4-cumylphenoxy, 4-(1,1,3,3-tetramethylbutyl)phenoxy, octylphenoxy, 4-tert-octylphenoxy, nonylphenoxy, dodecylphenoxy, octadecylphenoxy, pentadecylphenoxy, pentadecenylphenoxy, methoxyphenoxy, phenoxyphenoxy, benzyloxyphenoxy, n-hexyloxyphenoxy, 2-methoxyethylphenoxy, 4-(4'-oxyphenyl)-2,2,4-trimethylchroman, 2-(4'-oxyphenyl)-2,4,4-trimethylchroman, 1-(1-methyl-1-phenylethyl)-4-(1-methyl-1-(4'-oxyphenyl)ethyl)-benzene, 1,3-bis(1-methyl-1-phenylethyl)-5-(1-methyl-1-(4'-oxyphenyl)ethyl)-benzene, 4-cyanophenoxy, dialkylphenoxy, 2,6-dialkylphenoxy, 2,6-dimethylphenoxy, 2,6-di-t-butylphenoxy, 2,4-dialkylphenoxy, 2,4-di-t-butylphenoxy, 2,5-dialkylphenoxy, 2,5-di-t-butylphenoxy, 2,5-dicumylphenoxy, 3,5-dialkylphenoxy, 3,5-di-t-butylphenoxy, 3,5-dicumylphenoxy, 2,3-dialkylphenoxy, 2,3-di-t-butylphenoxy, dimethoxyphenoxy, halophenoxy, 4-halophenoxy, 4-bromophenoxy, dihalophenoxy, dibromophenoxy, 2,6-dihalophenoxy, 2,6-dibromophenoxy, 2,6-dichlorophenoxy, 2,6-(dialkoxycarbonyl)phenoxy, 2,6-(dimethoxycarbonyl)phenoxy, trialkylphenoxy, 2,3,6-trialkylphenoxy, 2,3,6-trimethylphenoxy, 2,4,6-trialkylphenoxy, 2,4,6-trimethylphenoxy, trihalophenoxy, tribromophenoxy, 2,4,6-trihalophenoxy, 2,4,6-tribromophenoxy, 2,4,6-trichlorophenoxy, vinyl, allyl, allyloxy, 2-allylphenoxy, 4-allylphenoxy, 4-ethenylphenoxy, cinnamyloxy, 4-allyl-2-methoxyphenoxy, propargyloxy, glycidoxy, and 4-oxymethyl-2-methoxy-2-methyl- 1,3-dioxolane, and wherein the resulting capped polycarbonate does not comprise a triazine-containing moiety as a structural unit in the polymer chain other than at a terminal site.

7. The process of claim 6 wherein the polycarbonate is derived from a melt reaction process with reactants comprising bisphenol A and diphenylcarbonate.

8. The process of claim 6 wherein $Z^1$ and $Z^2$ are each a 2,6-disubstituted aryloxy moiety.

9. A process for capping nucleophilic groups in a polymer which comprises combining and reacting the polymer with a triazine moiety, said moiety comprising at least one vinyl, allyl, or propargyloxy group or olefinic group of formula (VII; $Fu^1$):

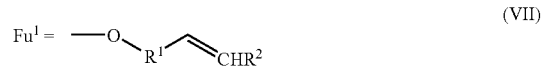

(VII)

wherein $R^1$ is an alkylene or arylene radical; and $R^2$ is hydrogen, alkyl or aryl, wherein the polymer is a poly(phenylene ether) comprising 2-6-dimethyl phenylene structural units.

* * * * *